United States Patent
Kamen et al.

(10) Patent No.: US 10,839,953 B2
(45) Date of Patent: Nov. 17, 2020

(54) PILL DISPENSER

(71) Applicant: DEKA Products Limited Partnership, Manchester, NH (US)

(72) Inventors: Dean Kamen, Bedford, NH (US); James G. Turner, Manchester, NH (US); Erik N. Sabin, Manchester, NH (US); Gregg W. Rivinius, Bedford, NH (US); David E. Collins, Amesbury, MA (US); Benjamin Zaslow, Brooklyn, NY (US); Jonathan Zobro, Grand Rapids, MI (US); Alexander R. Therrien, Zionsville, IN (US); Jared N. Farlow, Boston, MA (US)

(73) Assignee: DEKA Products Limited Partnership, Manchester, NH (US)

( * ) Notice: Subject to any disclaimer, the term of this patent is extended or adjusted under 35 U.S.C. 154(b) by 0 days.

(21) Appl. No.: 16/668,172

(22) Filed: Oct. 30, 2019

(65) Prior Publication Data

US 2020/0066388 A1 Feb. 27, 2020

Related U.S. Application Data

(63) Continuation of application No. 16/239,755, filed on Jan. 4, 2019, now Pat. No. 10,468,132, which is a
(Continued)

(51) Int. Cl.
*G16H 20/13* (2018.01)
*G06Q 50/22* (2018.01)
(Continued)

(52) U.S. Cl.
CPC ............ *G16H 20/13* (2018.01); *G06F 21/32* (2013.01); *G06K 9/00255* (2013.01);
(Continued)

(58) Field of Classification Search
CPC ............ G06F 19/3462; G06F 19/3418; G06F 19/3456; G07F 17/0092; G07F 11/002; G16H 20/13; G16H 20/17; G16H 70/40
See application file for complete search history.

(56) References Cited

U.S. PATENT DOCUMENTS

| | | |
|---|---|---|
| 4,336,882 A | 6/1982 | Sakwa |
| 4,460,106 A | 7/1984 | Moulding, Jr. et al. |

(Continued)

FOREIGN PATENT DOCUMENTS

| | | |
|---|---|---|
| WO | WO2008085607 A2 | 7/2008 |
| WO | WO2008112731 A2 | 9/2008 |

(Continued)

OTHER PUBLICATIONS

Landro, Laura. "Many Pills, Many Not Taken: Tracking Prescriptions with Technology, Personal Touch." The Wall Street Journal Oct. 10, 2011. Web. <http://www.wsj.com/articles/SB10001424052970203388804576616882856318782>.

(Continued)

*Primary Examiner* — Eric Blount
(74) *Attorney, Agent, or Firm* — James D. Wyninegar, Jr.

(57) ABSTRACT

A pill dispenser is disclosed that includes a pill-dispensing mechanism, a receptacle, an identifying camera positioned to capture an image of an area adjacent to the pill dispenser, and a processor in operative communication with the pill-dispensing mechanism and the identifying camera.

14 Claims, 15 Drawing Sheets

Related U.S. Application Data continuation of application No. 15/270,321, filed on Sep. 20, 2016, now Pat. No. 10,185,812, which is a continuation of application No. 15/077,389, filed on Mar. 22, 2016, now Pat. No. 9,465,919, which is a continuation of application No. 13/723,235, filed on Dec. 21, 2012, now Pat. No. 9,400,873, which is a continuation-in-part of application No. 13/333,574, filed on Dec. 21, 2011, now Pat. No. 10,453,157, and a continuation-in-part of application No. PCT/US2011/066588, filed on Dec. 21, 2011.

(60) Provisional application No. 61/679,117, filed on Aug. 3, 2012, provisional application No. 61/651,322, filed on May 24, 2012, provisional application No. 61/578,658, filed on Dec. 21, 2011, provisional application No. 61/578,649, filed on Dec. 21, 2011, provisional application No. 61/578,674, filed on Dec. 21, 2011.

(51) Int. Cl.
| | | |
|---|---|---|
| *G16H 10/60* | (2018.01) | |
| *G06F 21/32* | (2013.01) | |
| *G16H 40/63* | (2018.01) | |
| *H04N 5/225* | (2006.01) | |
| *G16H 20/17* | (2018.01) | |
| *G16H 20/10* | (2018.01) | |
| *G06K 9/00* | (2006.01) | |

(52) U.S. Cl.
CPC ............. *G06Q 50/22* (2013.01); *G16H 10/60* (2018.01); *G16H 20/10* (2018.01); *G16H 20/17* (2018.01); *G16H 40/63* (2018.01); *H04N 5/2257* (2013.01)

(56) References Cited

U.S. PATENT DOCUMENTS

| | | | |
|---|---|---|---|
| 4,485,925 A | 12/1984 | Fickert | |
| 4,524,869 A | 6/1985 | Nader | |
| 4,544,063 A | 10/1985 | Neward | |
| 4,784,288 A | 11/1988 | Jennings | |
| 4,785,932 A | 11/1988 | Checke | |
| 4,824,675 A | 4/1989 | Wong et al. | |
| 4,893,728 A | 1/1990 | Jennings et al. | |
| 4,903,860 A | 2/1990 | Leopoldi et al. | |
| 4,905,388 A | 3/1990 | Sinkow | |
| 4,905,866 A | 3/1990 | Bartell et al. | |
| 4,911,327 A | 3/1990 | Shepherd et al. | |
| 4,915,949 A | 4/1990 | Wong et al. | |
| 4,962,491 A | 10/1990 | Schaeffer | |
| 4,967,971 A | 11/1990 | Smith | |
| 4,974,729 A | 12/1990 | Steinnagel | |
| 5,014,798 A | 5/1991 | Glynn | |
| D348,101 S | 6/1994 | Poli | |
| 5,331,919 A | 7/1994 | Root et al. | |
| 5,372,267 A | 12/1994 | Hofmann | |
| 5,405,047 A | 4/1995 | Hansen | |
| 5,433,256 A | 7/1995 | Vasers | |
| 5,502,944 A | 4/1996 | Kraft et al. | |
| 5,579,933 A | 12/1996 | Hofmann | |
| 5,584,805 A | 12/1996 | Sutton | |
| 5,608,940 A | 3/1997 | Panyon | |
| 5,646,912 A * | 7/1997 | Cousin | A61J 7/0481 |
| | | | 368/10 |
| 5,660,138 A | 8/1997 | Hirsch | |
| 5,718,355 A | 2/1998 | Garby et al. | |
| 5,755,020 A | 5/1998 | Panyon | |
| 5,908,208 A | 6/1999 | Lapsker | |
| 5,921,394 A * | 7/1999 | Shroff | B65D 83/0454 |
| | | | 206/533 |
| 6,004,020 A | 12/1999 | Bartur | |
| 6,017,537 A | 1/2000 | Alexander et al. | |
| 6,220,480 B1 * | 4/2001 | Stankus | B65D 83/0409 |
| | | | 221/151 |
| 6,294,999 B1 | 9/2001 | Yarin | |
| 6,338,007 B1 | 1/2002 | Broadfield | |
| 6,529,446 B1 | 3/2003 | de la Huerga | |
| 6,535,637 B1 * | 3/2003 | Wootton | B65B 57/00 |
| | | | 382/190 |
| 6,694,334 B2 | 2/2004 | DuLong | |
| 6,976,628 B2 | 12/2005 | Krupa | |
| 7,061,831 B2 | 6/2006 | De La Huerga | |
| 7,537,005 B2 | 5/2009 | Dave | |
| 7,568,582 B1 | 8/2009 | Berger | |
| 7,630,789 B2 | 12/2009 | Broadfield | |
| 7,630,791 B2 | 12/2009 | Nguyen | |
| 7,658,736 B2 | 2/2010 | von Alten | |
| 7,673,771 B2 | 3/2010 | Bedore | |
| 7,715,277 B2 | 5/2010 | de la Huerga | |
| 7,747,454 B2 | 6/2010 | Bartfeld | |
| 7,753,085 B2 | 7/2010 | Tribble | |
| 7,814,731 B2 | 10/2010 | Bender | |
| 7,864,041 B2 | 1/2011 | Godlewski | |
| 7,978,564 B2 | 7/2011 | De La Huerga | |
| 8,061,351 B2 | 11/2011 | Dave | |
| 8,175,746 B2 | 5/2012 | Godlewski | |
| 8,234,008 B2 | 7/2012 | Weber | |
| 8,412,375 B2 | 4/2013 | Schifman | |
| D728,779 S | 5/2015 | Sabin et al. | |
| D735,319 S | 7/2015 | Sabin et al. | |
| D736,370 S | 8/2015 | Sabin et al. | |
| 9,151,646 B2 | 10/2015 | Kamen et al. | |
| D745,661 S | 12/2015 | Collins et al. | |
| D749,206 S | 2/2016 | Johnson et al. | |
| D751,689 S | 3/2016 | Peret et al. | |
| D751,690 S | 3/2016 | Peret et al. | |
| D752,209 S | 3/2016 | Peret et al. | |
| 9,295,778 B2 | 3/2016 | Kamen et al. | |
| D754,065 S | 4/2016 | Gray et al. | |
| D756,386 S | 5/2016 | Kendler et al. | |
| D758,399 S | 6/2016 | Kendler et al. | |
| D760,288 S | 6/2016 | Kendler et al. | |
| D760,289 S | 6/2016 | Kendler et al. | |
| 9,364,394 B2 | 6/2016 | Demers et al. | |
| 9,372,486 B2 | 6/2016 | Peret et al. | |
| D760,782 S | 7/2016 | Kendler et al. | |
| D760,888 S | 7/2016 | Gill et al. | |
| 9,400,873 B2 * | 7/2016 | Kamen | G06F 19/3462 |
| 9,408,966 B2 | 8/2016 | Kamen | |
| D767,756 S | 9/2016 | Sabin | |
| 9,435,455 B2 | 9/2016 | Peret et al. | |
| D768,716 S | 10/2016 | Kendler et al. | |
| 9,465,919 B2 | 10/2016 | Kamen et al. | |
| 9,488,200 B2 | 11/2016 | Kamen et al. | |
| D774,645 S | 12/2016 | Gill et al. | |
| 9,518,958 B2 | 12/2016 | Wilt et al. | |
| 9,636,455 B2 | 5/2017 | Kamen et al. | |
| D789,516 S | 6/2017 | Gill et al. | |
| 9,675,756 B2 | 6/2017 | Kamen et al. | |
| 9,677,555 B2 | 6/2017 | Kamen et al. | |
| 9,687,417 B2 | 6/2017 | Demers et al. | |
| D792,963 S | 7/2017 | Gill | |
| D795,424 S | 8/2017 | Sloss | |
| D795,805 S | 8/2017 | Gray et al. | |
| 9,719,964 B2 | 8/2017 | Blumberg | |
| 9,724,465 B2 | 8/2017 | Peret et al. | |
| 9,724,466 B2 | 8/2017 | Peret et al. | |
| 9,724,467 B2 | 8/2017 | Peret et al. | |
| 9,730,731 B2 | 8/2017 | Langenfeld et al. | |
| 9,744,300 B2 | 8/2017 | Kamen et al. | |
| 9,746,093 B2 | 8/2017 | Peret et al. | |
| 9,746,094 B2 | 8/2017 | Peret et al. | |
| 9,759,343 B2 | 9/2017 | Peret et al. | |
| 9,759,369 B2 | 9/2017 | Gray et al. | |
| 9,772,044 B2 | 9/2017 | Peret et al. | |
| D799,025 S | 10/2017 | Johnson et al. | |
| D801,519 S | 10/2017 | Sabin et al. | |
| 9,789,247 B2 | 10/2017 | Kamen et al. | |
| D802,118 S | 11/2017 | Peret et al. | |
| D803,386 S | 11/2017 | Sabin et al. | |

(56) References Cited

U.S. PATENT DOCUMENTS

| | | | |
|---|---|---|---|
| D803,387 S | 11/2017 | Bodwell et al. | |
| D804,017 S | 11/2017 | Sabin | |
| 9,808,572 B2 | 11/2017 | Kamen et al. | |
| D805,183 S | 12/2017 | Sabin et al. | |
| 9,856,990 B2 | 1/2018 | Peret et al. | |
| D813,376 S | 3/2018 | Peret et al. | |
| D814,021 S | 3/2018 | Sabin | |
| D815,730 S | 4/2018 | Collins et al. | |
| D816,685 S | 5/2018 | Kendler et al. | |
| D816,829 S | 5/2018 | Peret et al. | |
| D817,479 S | 5/2018 | Sabin et al. | |
| D817,480 S | 5/2018 | Sabin et al. | |
| 9,968,730 B2 | 5/2018 | Blumberg, Jr. et al. | |
| 9,976,665 B2 | 5/2018 | Peret et al. | |
| 10,044,791 B2 | 8/2018 | Kamen et al. | |
| 2002/0153411 A1 | 10/2002 | Wan et al. | |
| 2004/0094564 A1 | 5/2004 | Papp | |
| 2004/0104241 A1* | 6/2004 | Broussard | A61J 7/02 221/289 |
| 2004/0210341 A1 | 10/2004 | Wallace et al. | |
| 2005/0150488 A1 | 7/2005 | Dave | |
| 2005/0240305 A1 | 10/2005 | Bogash et al. | |
| 2006/0032923 A1 | 2/2006 | Krupa | |
| 2006/0088196 A1 | 4/2006 | Popovich | |
| 2006/0097000 A1 | 5/2006 | Gumpert | |
| 2006/0124656 A1 | 6/2006 | Popovich | |
| 2006/0140466 A1 | 6/2006 | Seshimo | |
| 2006/0200369 A1 | 9/2006 | Batch | |
| 2006/0218015 A1 | 9/2006 | Walker | |
| 2007/0156282 A1* | 7/2007 | Dunn | G06F 19/3462 700/244 |
| 2007/0265880 A1* | 11/2007 | Bartfeld | G07F 17/0092 705/2 |
| 2008/0000979 A1* | 1/2008 | Poisner | G06K 19/06046 235/462.01 |
| 2008/0056556 A1* | 3/2008 | Eller | G06F 19/3462 382/142 |
| 2008/0105588 A1 | 5/2008 | Tran | |
| 2008/0119958 A1 | 5/2008 | Bear et al. | |
| 2008/0294018 A1 | 11/2008 | Kurtz et al. | |
| 2009/0012818 A1* | 1/2009 | Rodgers | G01G 17/00 705/3 |
| 2009/0138122 A1 | 5/2009 | Wagner | |
| 2009/0167531 A1 | 7/2009 | Ferguson | |
| 2009/0224638 A1 | 9/2009 | Weber | |
| 2009/0276090 A1 | 11/2009 | Rajiv | |
| 2009/0295575 A1 | 12/2009 | Kennedy | |
| 2009/0299522 A1 | 12/2009 | Savir | |
| 2010/0038273 A1 | 2/2010 | Johnson | |
| 2010/0042430 A1 | 2/2010 | Bartfeld | |
| 2010/0076595 A1 | 3/2010 | Nguyen | |
| 2010/0140287 A1 | 6/2010 | Richardson et al. | |
| 2010/0215231 A1 | 8/2010 | Bartfeld | |
| 2010/0268380 A1 | 10/2010 | Waugh | |
| 2010/0318218 A1 | 12/2010 | Muncy, Jr. et al. | |
| 2011/0133948 A1 | 6/2011 | Ervin et al. | |
| 2011/0160901 A1 | 6/2011 | Abrams, Jr. et al. | |
| 2011/0264033 A1 | 10/2011 | Jensen | |
| 2011/0303692 A1 | 12/2011 | Kim | |
| 2011/0313789 A1 | 12/2011 | Kamen et al. | |
| 2012/0004764 A1 | 1/2012 | Rahilly | |
| 2012/0004772 A1 | 1/2012 | Rahilly | |
| 2012/0029693 A1 | 2/2012 | Bear et al. | |
| 2012/0109071 A1 | 5/2012 | Larsen et al. | |
| 2012/0185267 A1 | 7/2012 | Kamen | |
| 2012/0187143 A1 | 7/2012 | Weber | |
| 2012/0187815 A1 | 7/2012 | Weber | |
| 2012/0191241 A1 | 7/2012 | Rahilly | |
| 2012/0313785 A1 | 12/2012 | Hanson et al. | |
| 2012/0330684 A1 | 12/2012 | Jacobs et al. | |
| 2013/0030566 A1 | 1/2013 | Shavelsky et al. | |
| 2013/0110283 A1* | 5/2013 | Baarman | A61J 7/0084 700/236 |
| 2013/0177455 A1 | 7/2013 | Kamen | |
| 2013/0182381 A1 | 7/2013 | Gray et al. | |
| 2013/0184676 A1 | 7/2013 | Kamen | |
| 2013/0188040 A1 | 7/2013 | Kamen | |
| 2013/0191513 A1 | 7/2013 | Kamen | |
| 2013/0197693 A1* | 8/2013 | Kamen | G06F 21/32 700/244 |
| 2013/0204188 A1 | 8/2013 | Kamen | |
| 2013/0253699 A1 | 9/2013 | Reimer | |
| 2013/0272773 A1 | 10/2013 | Kamen | |
| 2013/0281965 A1 | 10/2013 | Kamen | |
| 2013/0297330 A1 | 11/2013 | Kamen et al. | |
| 2013/0299381 A9 | 11/2013 | Luciano, Jr. | |
| 2013/0310990 A1 | 11/2013 | Peret et al. | |
| 2013/0317753 A1 | 11/2013 | Kamen | |
| 2013/0317837 A1 | 11/2013 | Ballantyne | |
| 2013/0336814 A1 | 12/2013 | Kamen | |
| 2013/0339049 A1 | 12/2013 | Blumberg, Jr. | |
| 2013/0346108 A1 | 12/2013 | Kamen | |
| 2014/0046676 A1 | 2/2014 | Kibler et al. | |
| 2014/0143064 A1 | 5/2014 | Tran | |
| 2014/0165703 A1 | 6/2014 | Wilt | |
| 2014/0168453 A1 | 6/2014 | Shoemake et al. | |
| 2014/0180711 A1 | 6/2014 | Kamen | |
| 2014/0188076 A1 | 7/2014 | Kamen | |
| 2014/0188516 A1* | 7/2014 | Kamen | G16H 20/17 705/3 |
| 2014/0195639 A1 | 7/2014 | Kamen | |
| 2014/0227021 A1 | 8/2014 | Kamen | |
| 2014/0318639 A1 | 10/2014 | Peret | |
| 2014/0337045 A1 | 11/2014 | Scrivner et al. | |
| 2014/0343492 A1 | 11/2014 | Kamen | |
| 2014/0354435 A1 | 12/2014 | Hanson et al. | |
| 2015/0002667 A1 | 1/2015 | Peret et al. | |
| 2015/0002668 A1 | 1/2015 | Peret et al. | |
| 2015/0002677 A1 | 1/2015 | Peret et al. | |
| 2015/0033823 A1 | 2/2015 | Blumberg, Jr. | |
| 2015/0314083 A1 | 4/2015 | Blumberg, Jr. et al. | |
| 2015/0154364 A1 | 6/2015 | Biasi et al. | |
| 2015/0157791 A1 | 6/2015 | Desch et al. | |
| 2015/0238228 A1 | 8/2015 | Langenfeld et al. | |
| 2015/0257974 A1 | 9/2015 | Demers et al. | |
| 2015/0332009 A1 | 11/2015 | Kane et al. | |
| 2016/0055397 A1 | 2/2016 | Peret et al. | |
| 2016/0055649 A1 | 2/2016 | Peret et al. | |
| 2016/0061641 A1 | 3/2016 | Peret et al. | |
| 2016/0063353 A1 | 3/2016 | Peret et al. | |
| 2016/0073063 A1 | 3/2016 | Peret et al. | |
| 2016/0084434 A1 | 3/2016 | Janway et al. | |
| 2016/0097382 A1 | 4/2016 | Kamen et al. | |
| 2016/0131272 A1 | 5/2016 | Yoo | |
| 2016/0158437 A1 | 6/2016 | Biasi et al. | |
| 2016/0179086 A1 | 6/2016 | Peret et al. | |
| 2016/0184510 A1 | 6/2016 | Kamen et al. | |
| 2016/0203292 A1 | 7/2016 | Kamen et al. | |
| 2016/0262977 A1 | 9/2016 | Demers et al. | |
| 2016/0319850 A1 | 11/2016 | Kamen et al. | |
| 2016/0346056 A1 | 12/2016 | Demers et al. | |
| 2016/0362234 A1 | 12/2016 | Peret et al. | |
| 2017/0011202 A1 | 1/2017 | Kamen et al. | |
| 2017/0045478 A1 | 2/2017 | Wilt et al. | |
| 2017/0216516 A1 | 8/2017 | Dale et al. | |
| 2017/0224909 A1 | 8/2017 | Kamen et al. | |
| 2017/0259230 A1 | 9/2017 | Demers et al. | |
| 2017/0266378 A1 | 9/2017 | Kamen et al. | |
| 2017/0268497 A1 | 9/2017 | Kamen et al. | |
| 2017/0284968 A1 | 10/2017 | Blumberg, Jr. | |
| 2017/0296745 A1 | 10/2017 | Kamen et al. | |
| 2017/0303969 A1 | 10/2017 | Langenfeld et al. | |
| 2017/0321841 A1 | 11/2017 | Gray et al. | |
| 2017/0333623 A1 | 11/2017 | Kamen et al. | |
| 2017/0335988 A1 | 11/2017 | Peret et al. | |
| 2018/0038501 A1 | 2/2018 | Peret et al. | |
| 2018/0066648 A1 | 3/2018 | Kamen et al. | |
| 2018/0080605 A1 | 3/2018 | Janway et al. | |

(56) References Cited

U.S. PATENT DOCUMENTS

| | | |
|---|---|---|
| 2018/0106246 A1 | 4/2018 | Kamen et al. |
| 2018/0128259 A1 | 5/2018 | Kamen et al. |

FOREIGN PATENT DOCUMENTS

| | | | |
|---|---|---|---|
| WO | WO2013095459 A9 | 6/2013 | |
| WO | WO2013096713 A2 | 6/2013 | |
| WO | WO2013096718 A2 | 6/2013 | |
| WO | WO2013096722 A2 | 6/2013 | |
| WO | WO2013096909 A2 | 6/2013 | |
| WO | WO2013176770 A2 | 11/2013 | |
| WO | WO2013177357 A1 | 11/2013 | |
| WO | WO2014100557 A2 | 6/2014 | |
| WO | WO2014100571 A2 | 6/2014 | |
| WO | WO2014100658 A1 | 6/2014 | |
| WO | WO2014100687 A2 | 6/2014 | |
| WO | WO2014100736 A2 | 6/2014 | |
| WO | WO2014100744 A2 | 6/2014 | |
| WO | WO2014144557 A2 | 9/2014 | |
| WO | WO2015017275 A1 | 2/2015 | |

OTHER PUBLICATIONS

International Search Report & Written Opinion dated Jun. 14, 2013, received in International patent application No. PCT/US2012/071131 (J74WO), 15 pgs.

"MedSmart PLUS Monitored Automatic Medication Pill Dispenser." Philips Medication Dispenser. Web. Nov. 15, 2011. <http://www.epill.com/philipsmd.html>.

Notice of Reason for Rejection dated Jul. 7, 2015 for Japanese Application No. 2014-548932.

Invitation to Respond to Written Opinion, Search Report, and Written Opinion for Singapore Patent Application 11201403514S dated Mar. 19, 2015.

Invitation to Respond to Written Opinion and second Written Opinion for Singapore Patent Application 11201403514S dated Oct. 16, 2015.

International Preliminary Report on Patentability dated Jul. 3, 2014, received in International patent application No. PCT/US2012/071131, 10 pgs.

Decision to Grant for Japanese Patent Application 2014-548932, 3 pgs., dated Feb. 9, 2016.

European First Examiniation Report dated May 3, 2016, received in European patent application No. 12 826 588.1-1958, 5 pgs.

U.S. Appl. No. 61/578,674 filed Dec. 21, 2011.

PCT/US12/71131 filed Dec. 21, 2012, Application Publication WO2013096718A1.

U.S. Appl. No. 13/723,235 filed Dec. 21, 2012, Application Publication US20130197693A1.

U.S. Appl. No. 15/077,389 filed Mar. 22, 2016, Application Publication US20160203292A1.

U.S. Appl. No. 15/270,321 filed Sep. 20, 2016, Application Publication US20170011202A1.

U.S. Appl. No. 16/239,755 filed Jan. 4, 2019, Application Publication US20190139640A1.

* cited by examiner

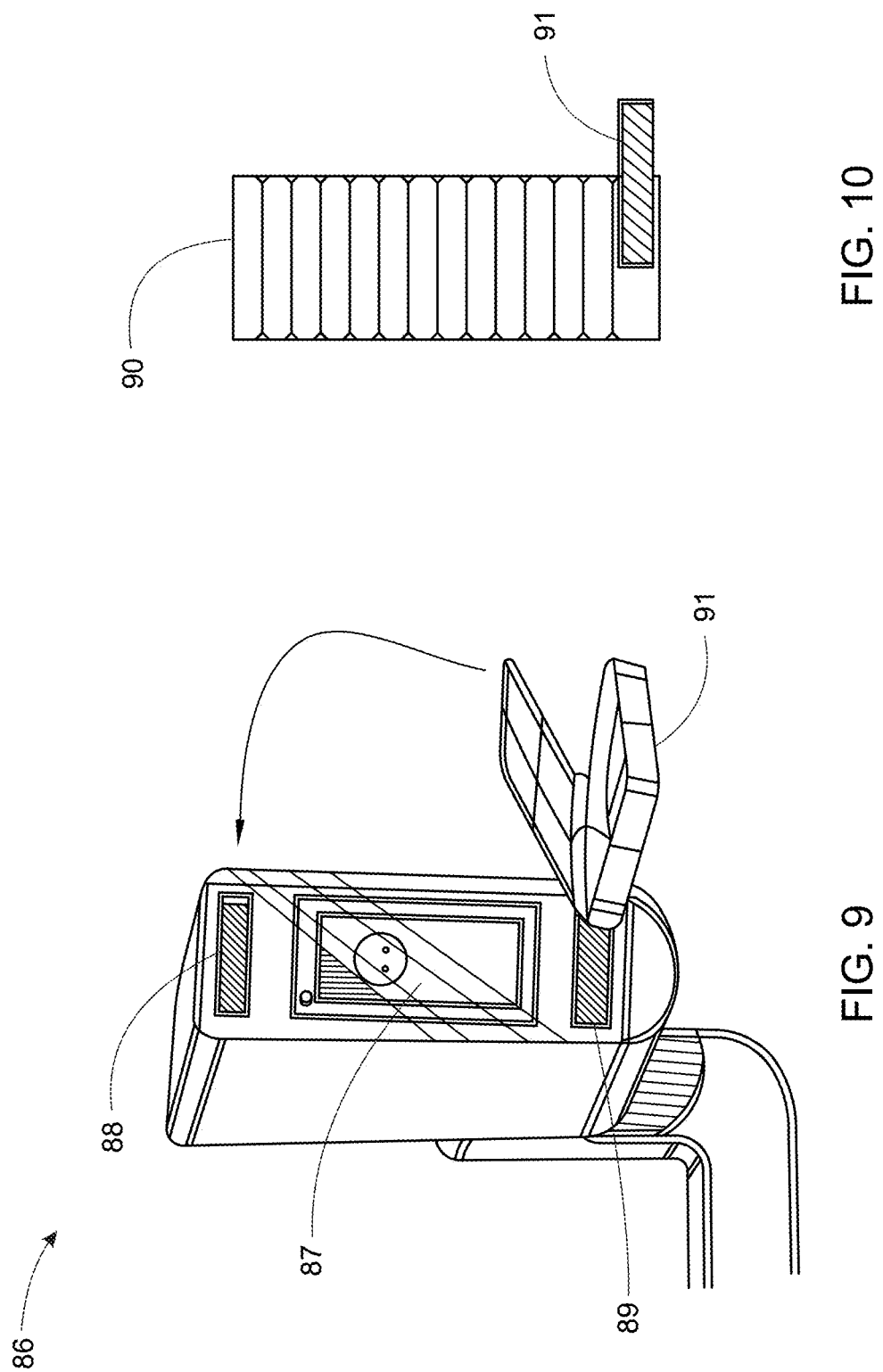

PILL DISPENSER

CROSS REFERENCE TO RELATED APPLICATIONS

This application is a continuation application of U.S. patent application Ser. No. 16/239,755, filed Jan. 4, 2019 and entitled Pill Dispenser, now U.S. Publication No. US-2019-0139640-A1, published May 9, 2019 which is a continuation application of U.S. patent application Ser. No. 15/270,321, filed Sep. 20, 2016 and entitled Pill Dispenser, now U.S. Pat. No. 10,185,812, issued Jan. 22, 2019 which is a continuation application of U.S. patent application Ser. No. 15/077,389, filed Mar. 22, 2016 and entitled Pill Dispenser, now U.S. Pat. No. 9,465,919, issued Oct. 11, 2016.

U.S. patent application Ser. No. 15/077,389, filed Mar. 22, 2016 and entitled Pill Dispenser, now U.S. Pat. No. 9,465,919, issued Oct. 11, 2016 is a continuation application of U.S. patent application Ser. No. 13/723,235, filed Dec. 21, 2012 and entitled System, Method, and Apparatus for Dispensing Oral Medications, now U.S. Pat. No. 9,400,873, issued Jul. 26, 2016 which is a Non-Provisional Application which claims priority to and benefit of the following:

U.S. Provisional Patent Application Ser. No. 61/578,649, filed Dec. 21, 2011 and entitled System, Method, and Apparatus for Infusing Fluid;

U.S. Provisional Patent Application Ser. No. 61/578,658, filed Dec. 21, 2011 and entitled System, Method, and Apparatus for Estimating Liquid Delivery;

U.S. Provisional Patent Application Ser. No. 61/578,674, filed Dec. 21, 2011 and entitled System, Method, and Apparatus for Dispensing Oral Medications;

U.S. Provisional Patent Application Ser. No. 61/679,117, filed Aug. 3, 2012 and entitled System, Method, and Apparatus for Monitoring, Regulating, or Controlling Fluid Flow; and U.S. Provisional Patent Application Ser. No. 61/651,322, filed May 24, 2012 and entitled System, Method, and Apparatus for Electronic Patient Care, each of which is hereby incorporated herein by reference in its entirety.

U.S. patent application Ser. No. 13/723,235, filed Dec. 21, 2012 and entitled System, Method, and Apparatus for Dispensing Oral Medications is also a Continuation In Part Application of the following:

U.S. patent application Ser. No. 13/333,574, filed Dec. 21, 2011 and entitled System, Method, and Apparatus for Electronic Patient Care, now U.S. Publication No. US-2012-0185267-A1, published Jul. 19, 2012, and PCT Application Serial No. PCT/US11/66588, filed Dec. 21, 2011 and entitled System, Method, and Apparatus for Electronic Patient Care, both of which are hereby incorporated herein by reference in their entireties.

U.S. patent application Ser. No. 15/270,321, filed Sep. 20, 2016 and entitled Pill Dispenser, now U.S. Pat. No. 10,185,812, issued Jan. 22, 2019 may also be related to one or more of the following patent applications filed on Dec. 21, 2012, all of which are hereby incorporated herein by reference in their entireties:

Nonprovisional application for System, Method, and Apparatus for Clamping, Ser. No. 13/723,238;

PCT application for System, Method, and Apparatus for dispensing oral medications, Ser. No. PCT/US12/71131;

Nonprovisional application for Syringe Pump, Ser. No. 13/724,568;

Nonprovisional application for System, Method, and Apparatus for Infusing Fluid, Ser. No. 13/725,790;

PCT application for System, Method, and Apparatus for Infusing Fluid, Ser. No. PCT/US12/71490;

Nonprovisional application for System, Method, and Apparatus for Electronic Patient Care, Ser. No. 13/723,239;

Nonprovisional application for System, Method, and Apparatus for Electronic Patient Care, Ser. No. 13/723,242;

Nonprovisional application for System, Method, and Apparatus for Monitoring, Regulating, or Controlling Fluid Flow, Ser. No. 13/723,244;

PCT application for System, Method, and Apparatus for Monitoring, Regulating, or Controlling Fluid Flow, Serial No. PCT/US12/71142;

Nonprovisional application for System, Method, and Apparatus for Estimating Liquid Delivery, Ser. No. 13/723,251;

PCT application for System, Method, and Apparatus for Estimating Liquid Delivery, Serial No. PCT/US12/71112; and Nonprovisional application for System, Method, and Apparatus for Electronic Patient Care, Ser. No. 13/723,253.

BACKGROUND

Relevant Field

The present disclosure relates to dispensing oral medications. More particularly, the present disclosure relates to a system, method, and apparatus for dispensing oral medications.

Description of Related Art

Medications are taken for many different reasons, such as to treat an illness, relieve pain, keep biological parameters within low risk ranges (e.g., blood pressure), nutritional supplementation, and other reasons. The medication may be taken for a short period of time or for life. For example, a person with an ear infection may get a prescription for a certain medication to take for a week. Other times the medication is taken for a long period of time, possibly forever. For example, a person with high blood pressure may take a certain medication all the time. People taking medication for a long period of time may receive a prescription for a certain quantity of the medication given to the patient by a pharmacists or physician with possibly one or more refills. After the prescription expires (e.g., all refills are used) the person, or someone caring for them, may need to call a doctor or caregiver to receive a new prescription. Some medications are given in pill form, which is typically a small capsule of medication designed to be taken orally or may be a suppository. A pill for the purposes of these descriptions may be a prescription drug, an over-the-counter medication, a vitamin, a nutritional supplement, or any other tablet like object which is designed to be taken by the user.

The status of the prescription needs to be tracked to ensure that the prescription doesn't expire. A doctor's appointment may be necessary to get the prescription renewed (or possibly modified). Depending on the type of insurance, the medication, and/or the pharmacy (e.g., brick-and-mortar, mail order, etc.), the prescription may need to be filled in advance of the time that the medication will be needed.

Many users need to take a variety of different medications. The medications may need to be taken at different times (e.g., days, hours, etc.) and in different quantities. Medication organizers are utilized to assist in tracking the medications that they need to take. The organizers may come in various styles. For example, they may include containers where each container includes the medication that they take for a certain period (e.g., hour, day, etc.).

Certain prescriptions may require the user to monitor and/or measure certain body parameters (e.g., blood sugar) and to bring these parameters to the doctor for review when it is time to renew or modify the prescription. This may require the user to keep detailed records and remember to bring them to the doctor. Some users may have limited mobility so that getting to the pharmacy to get a prescription filled or getting to the doctor to provide the tracked parameters may be a hardship.

SUMMARY

In one aspect of the present disclosure, a pill dispenser includes a housing, a pill-dispensing mechanism, a receptacle, a first pill-viewing camera, an identifying camera, one or more processors, and a storage medium. The housing defines an opening. The pill-dispensing mechanism is disposed within the housing and is operatively coupled to the opening. The receptacle is operatively coupled to the housing. The receptacle may be a cup holder configured to receive a cup. The first pill-viewing camera is positioned to capture an image of the receptacle. The identifying camera is positioned to capture an image of an area adjacent to the housing. The identifying camera may be a panning camera. The storage medium may include instructions for identifying a face (e.g., the position of the face) as indicated by the panning camera and panning the camera towards the face to center the face. The one or more processors are in operative communication with the pill-dispensing mechanism, the first pill-viewing camera, and the identifying camera.

The storage medium stores one or more processor-executable instructions (e.g., executable by the one or more processors) for: instructing the pill-dispensing mechanism to dispense a pill; instructing the first pill-viewing camera to capture a first image of the pill; determining a presence of the pill within the first image; instructing the first pill-viewing camera to capture a second image; determining an absence of the pill within the second image; and instructing the identifying camera to capture a third image. In some specific embodiments, the presence of the pill within the first image (e.g., the image of the pill is within the first image) and the absence of the pill within the second image (e.g., the image of the pill is not within the second image) may be used to determine compliance (e.g., presence and absence within a time frame may be considered as compliance and/or may be a prerequisite for a determination of compliance). The storage medium may include instructions for identifying an authorized user and the pill within the third image to determine compliance, identifying an authorized user and a bottom of a cup within the third image to determine compliance, and/or decoding a bar code within the third image.

In another aspect of the present disclosure, the pill dispenser is configured for insertion into a dock. The dock may supply power to the pill dispenser and a communications link to a monitoring client.

In another aspect of the present disclosure, the storage medium further comprises processor-executable instructions configured for execution by the at least one processor for determining compliance has occurred if the first image includes an image of the pill and the second image does not include another image of the pill.

The storage medium may include instructions for instructing the identifying camera to capture the third image after a predetermined amount of time after the pill is dispensed by the pill-dispensing mechanism.

In another aspect of the present disclosure, the pill dispenser includes a button operatively coupled to the housing. The button is in operative communication with the one or more processors. The storage medium may further include instructions for dispensing the pill only when the button is pressed and/or for instructing the identifying camera to capture the third image when the button is pressed (e.g., to capture an image of the person pressing the button, for example). Additionally or alternatively, the storage medium may include instructions for instructing the identifying camera to capture a plurality of images including the third image in accordance with a predetermined schedule when the button is pressed. The unauthorized user may be determined during an authorization algorithm to authorize the dispensing of the pill.

In yet another aspect of the present disclosure, the storage medium may include instructions for instructing the identifying camera to capture a series of images until the at least one processor identifies the presence of at least one face in a captured image of the series of captured images when the button is pressed. The storage medium may include instructions for issuing an alert in response to the determined unauthorized user.

The storage medium may include instructions for determining that a face within the third image is an unauthorized user and communicating the third image and an indication that the unauthorized user is within the third image to a server.

The pill dispenser may include a storage medium having instructions for storing the third image in the storage medium and/or encrypting the third image within the storage medium. The third image may be encrypted using a public key of a pair of asymmetrical encryption keys. The encrypted third image may be communicated to a server via a communication component of the pill dispenser.

In another aspect of the present disclosure, the storage medium may include instructions for determining whether a face within the third image is an authorized user and communicating the third image to a server with an indication of whether the face within the third image is authorized.

In yet another aspect, the pill dispenser includes a speaker disposed within the housing. The one or more processors may be in communication with the speaker (e.g., to control the speaker). The storage medium may include instructions for instructing the speaker to audibly sound a reminder when the second image includes the pill and a predetermined amount of time has elapsed. Additionally or alternatively, the storage medium may include instructions for playing a user recorded message to remind a patient to take the pill.

In some aspects of the present disclosure, the storage medium may include instructions for identifying the pill using the first image. The pill may be identified based on a color of the pill, a shape of the pill, characters on the pill, and a plurality of colors of the pill. Additionally or alternatively, the pill may be based upon an estimated weight from a scale integrated into the receptacle. The processor may estimate the weight of the pill by subtracting an estimated weight of a cup disposed within the receptacle.

In yet another aspect of the present disclosure, the pill dispenser includes a second pill-viewing camera positioned to capture an image of the pill, e.g., through a transparent cup bottom. The second pill-viewing camera may be disposed within the receptacle and/or coupled to the receptacle. The storage medium may include instructions for instructing the second pill-viewing camera to capture a fourth image including the pill and identifying the pill using the first and fourth images. The one or more processors may identify the pill using at least one of a color of the pill, a shape of the pill, characters on the pill, and a plurality of colors of the pill as determined using the first and fourth images. For example, a pill may have three colors that distinguish it as compared to all other known pills; if one or more of the pill-viewing cameras identify all three colors, the processor may use those identified three colors to determine the type of pill.

In yet another aspect of the present disclosure, the storage medium may include instructions for instructing the second pill-viewing camera to capture a fourth image including the pill and determining compliance utilizing the first and fourth images of the pill.

In yet an additional aspect of the present disclosure, the pill dispenser may also include a touch screen. The one or more processors may be in operative communication with the touch screen. The storage medium may include instructions for instructing the touch screen to display a pre-stored image of a prescribed pill on the touch screen about when the at least one processor instructs the pill-dispensing mechanism to dispense the pill.

The storage medium may further comprise processor-executable instructions configured for execution by the at least one processor for instructing the touch screen to display a user-selectable prompt requesting user confirmation that the pre-stored image of the prescribed pill on the touch screen matches the dispensed pill.

In yet another aspect of the present disclosure, the pill dispenser may include a speaker disposed within the housing. The one or more processors may be in operative communication with the speaker. The storage medium may include instructions for instructing the speaker to audibly sound a reminder when a predetermined amount of time has passed and no user confirmation of the user-selectable prompt has occurred.

In yet an additional aspect of the present disclosure, the storage medium may include instructions for instructing the pill-dispensing mechanism to dispense a plurality of pills in accordance with a predetermined schedule. The pill-dispensing mechanism may automatically dispense the plurality of pills when each respective pill is scheduled for being dispensed according to the predetermined schedule.

The storage medium may include instructions to log a determined compliance and store a log entry in the storage medium. The log entry may include at least one of voice data of a user used to authenticate the user, an image of the user used to authenticate the user, an image of the pill from the first pill-viewing camera, an image of the pill from a second pill-viewing camera, a location of the pill-dispensing mechanism, a time stamp, a date stamp, a patient ID from an RFID tag, a nurse ID from another RFID tag, an ambient temperature value, and/or an ambient light value.

In another aspect of the present disclosure, the pill dispenser includes a biometric identification component in operative communication with the one or more processors. The storage medium may include instructions for authenticating a user using biometric data from the biometric identification component. The biometric identification component is one of a microphone, a camera, a fingerprint scanner, a hand scanner, an iris scanner, and a retina scanner. Additionally, in some embodiments, the storage medium may include instructions for: communicating with a server having electronic medical records stored therein using the communication component; querying an electronic medical record entry of the server; and determining if the biometric data from the biometric identification component corresponds to the user as indicated by the electronic medical records.

In another aspect of the present disclosure, the pill dispenser includes a microphone and a speaker in operative communication with the one or more processors. The storage medium may include instructions for: instructing the speaker to play an audio recording requesting a sequence of words be spoken; recording sound using the microphone; and authenticating a user in accordance with the sound, wherein the at least one processor authenticates the user when a voice in the sound corresponds to an authorized user.

The storage medium may include instructions for communicating with a server having electronic medical records stored therein using the communication component; querying an electronic medical record entry of the electronic medical records of the server for at least one authorized user of the pill dispenser; and determining if a voice in the recorded sound corresponds to a user of the at least one authorized user as indicated by the electronic medical records entry.

In yet another aspect of the present disclosure, the pill dispenser may include a scanner configured to identify a user and/or determine if the user is an authorized user. The scanner may be one of a barcode scanner, a camera adapted to read a barcode, an RFID transponder, and/or a laser barcode scanner.

In yet another aspect of the present disclosure, the pill dispenser includes a communication component, e.g., a transceiver, in operative communication with the one or more processors. The storage medium may include instructions for relaying data from a patient-care device to a server using the communication component.

In yet another aspect of the present disclosure, the pill-dispensing mechanism may be coupled to one or more one pill cartridges (e.g., three) each configured to dispense a plurality of pills. The pill cartridge may include a memory preprogrammed with a dispensing schedule. The memory is in operative communication with the processor. The memory may be part of the computer-readable medium or is separate therefrom.

In yet another aspect of the present disclosure, the pill dispenser includes a button operatively coupled to the housing and in operative communication with the one or more processors. The storage medium may include instructions for: alerting a user of a scheduled pill dispense in accordance with a predetermined schedule; authenticating the user; instructing the pill-dispensing mechanism to dispense a pill in accordance with the scheduled pill dispense when the button is pressed and the user is authorized; and determining compliance of the scheduled pill dispense.

The alert may include an audible sound from a speaker that includes a reminder that the scheduled pill dispense has occurred in accordance with the predetermined schedule.

In yet another aspect of the present disclosure, the pill dispenser includes a speaker disposed within the housing and a global positioning system component. The one or more processors may be in operative communication with the speaker and the global positioning system component. The global positioning system component determines a position of the pill dispenser and communicates the position to the one or more processors (e.g., directly or through a memory, such as the computer-readable medium). The storage medium may include instructions for: determining if the position of the pill dispenser is within a predetermined authorized area as determined by the global positioning system component; and instructing the speaker to audibly sound an alert that the pill dispenser is outside the predetermined authorized area.

In yet another aspect of the present disclosure, the pill dispenser includes a communication component in operative communication with the one or more processors and the global positioning system component both operatively coupled to the one or more processors. The global positioning system component is configured to determine a position of the pill dispenser. The storage medium may include instructions for: determining if the position of the pill dispenser is within a predetermined authorized area as determined by the global positioning system component; and communicating to a server that the pill dispenser is outside the predetermined authorized area via the communication component.

In another aspect of the present disclosure, the pill dispenser includes a communication component and a global positioning system component both in operative communication with the one or more processors. The storage medium may include instructions for communicating to a server the position of the pill dispenser via the communication component.

The storage medium may include instructions for: determining a position of the pill dispenser via the global positioning system component; determining a position of a user; and dispensing a pill only when the pill dispenser and a user are within a predetermined distance between each other.

The pill dispenser may have a removable screen and/or a communication module may be attachable to the pill dispenser. In some embodiments, several communication modules are attachable to the pill dispenser and/or are attachable together and then attachable to the pill dispenser.

In yet another aspect of the present disclosure, the pill dispenser includes a non-volatile memory in operative communication with the one or more processors. The one or more processors can store one or more operating parameters within the non-volatile memory thereby allowing the pill dispenser to recover from a power failure. For example, the one or more processors can store the dispensing schedule and an inventory of the pills within the pill cartridges within the non-volatile memory.

In yet another aspect of the present disclosure, the pill dispenser includes a scanner configured to identify a prescription. The scanner is one of a barcode scanner, a camera adapted to read a barcode, an RFID transponder, and a laser barcode scanner.

In yet another aspect of the present disclosure, the pill dispenser includes a wireless-power receiver configured to receive wireless power and power at least one circuit within the pill dispenser.

In yet another aspect of the present disclosure, a bill is electronically communicated via a transceiver to a transaction server when a pill is dispensed.

In yet another aspect of the present disclosure, the pill dispenser includes an RFID interrogator. The storage medium may include instructions to store a log entry in an RFID tag via the RFID interrogator. The log entry may include one or more of voice data of a user used to authenticate the user, an image of the user used to authenticate the user, an image of the pill from the first pill-viewing camera, an image of the pill from a second pill-viewing camera, a location of the pill-dispensing mechanism, a time stamp, a date stamp, a patient ID from an RFID tag, a nurse ID from another RFID tag, an ambient-temperature value, and/or an ambient-light value.

In yet another aspect of the present disclosure, the pill dispenser is in operative communication with one or more patient-care devices. The pill dispenser may monitor one or more patient-care parameters to determine the efficacy of the pills being dispensed. Additionally or alternatively, the pill dispenser may upload the one or more patient-care parameters to a server that can determine efficacy of the pill.

In yet another aspect of the present disclosure, the pill dispenser includes a communication component in operative communication with the one or more processors. The storage medium may include instructions for relaying a patient-care parameter from a patient-care device via the communication component.

In yet another aspect of the present disclosure, a pill dispenser includes a housing, a pill-dispensing mechanism, a display, one or more processors, and a storage medium. The housing defines an opening. The pill-dispensing mechanism is disposed within the housing and is operatively coupled to the opening. The one or more processors are in operative communication with the pill-dispensing mechanism and the display. The storage medium stores processor-executable instructions configured for execution by the one or more processors for displaying a graphic illustrating an image of a patient taking a pill. The graphic may be illustrated after a button is pressed and/or after a pill is dispensed.

In yet another aspect of the present disclosure, a pill dispenser includes a housing, a pill-dispensing mechanism, a communication component, such as a transceiver, one or more processors, and a storage medium. The housing defines an opening. The pill-dispensing mechanism is disposed within the housing and is operatively coupled to the opening. The one or more processors are in operative communication with the pill-dispensing mechanism and the communication component. The storage medium stores processor-executable instructions configured for execution by the one or more processors for determining if one or more pills within the housing are contraindicated as determined via at least one of an electronic medical record and a drug error reduction system accessed via the communication component.

In yet another aspect of the present disclosure, a system for dispensing oral medications includes a pill dispenser and a monitoring client. The monitoring client may communicate a pill dispensing schedule to the pill dispenser.

In yet another aspect of the present disclosure, a system for dispensing oral medications includes a pill dispenser configured to dispense a pill and a plurality of monitoring clients in operative communication with the pill dispenser. A monitoring client of the plurality of monitoring clients is authorized to communicate a pill dispensing schedule to the pill dispenser.

In an aspect of the present disclosure, a system for dispensing oral medications includes a pill dispenser configured to dispense a pill and a monitoring client in operative communication with the pill dispenser. The monitoring client may receive one or more images from the pill dispenser. The monitoring client may communicate one or more dispense commands to the pill dispenser thereby causing the pill dispenser to dispense the pill. The monitoring client may authorize a user using a camera and may communicate at least one dispense command to the pill dispenser in response to the authorized user. The monitoring client may authorize a user using a microphone and may communicate one or more dispense commands to the pill dispenser in response to the authorized user.

The monitoring client may be an authorized monitoring client of a plurality of monitoring clients. The user interface of the monitoring client may be used to associate the monitoring client with one or more pill dispensers to monitor the pill dispenser and/or to send email, text messages, or other messages to the pill dispensers, etc. For example, the pill dispenser may be used to create an address book of pill dispensers to monitor the operation of the pill dispensers (e.g., compliance and/or dosage tracking), to communicate with the pill dispensers, and/or to determine which patients associated with each of the pill dispensers is non-compliant. The pill dispenser may communicate compliance data to the monitoring client. The monitoring client can update a prescription and communicate the updated prescription to the pill dispenser wherein the pill dispenser modifies a pill dispensing schedule in accordance with the updated prescription. The pill dispenser may communicate an electronic message to the monitoring client when the pill dispenser determines that non-compliance has occurred. One of the pill dispenser and the monitoring client may initiate two-way communications when the pill dispenser determines that non-compliance has occurred. The monitoring client can display a calendar displaying compliant days and non-compliant days.

In yet another aspect of the present disclosure, a system for dispensing oral medications includes a pill dispenser configured to dispense a pill, an audio/visual device in operative communication with the pill dispenser, and a monitoring client in operative communication with the pill dispenser. The pill dispenser and the monitoring client are configured for two-way communications, and the pill dispenser utilizes the audio/visual device in the two-way communications.

In yet another aspect of the present disclosure, a system for dispensing oral medications includes a plurality of pill dispensers each having a camera, a server for receiving at least one image from each camera, and a terminal for displaying the at least one image for user determination of compliance.

In yet another aspect of the present disclosure, a system for dispensing oral medications includes a pill dispenser and a monitoring client having a camera. The monitoring client is configured to capture an image of a pill to identify the pill and communicate the identified pill to at least one of a server and the pill dispenser.

The server and/or the pill dispenser determines if the pill meets predetermined safety criteria in accordance with one or more pills scheduled for being dispensed by the pill dispenser. The monitoring client compares the identified pill with a schedule to determine compliance. The monitoring client logs the determined compliance.

In yet another aspect of the present disclosure, a system includes a pill dispenser and a monitoring client having a scanner. The monitoring client is configured to scan a label (e.g., of a bottle of pills) to identify a medication and/or a prescription. The monitoring client can communicate the identified pill or prescription to a server and/or the pill dispenser. The server and the pill dispenser is configured to determine if the pill meets predetermined safety criteria in accordance with one or more pills scheduled for being dispensed by the pill dispenser.

In yet another aspect of the present disclosure, a system for dispensing oral medications includes a pill dispenser and a monitoring client. The monitoring client issues a reminder to take a pill dispensed by the pill dispenser. The monitoring client is in operative communication with the pill dispenser to determine if the pill has been taken, and the monitoring client issues another reminder if the pill has not been taken after a predetermined amount of time.

The monitoring client can execute a compliance determination algorithm. Compliance may be determined by viewing a camera on the pill dispenser from the monitoring client; by patient confirmation on the pill dispenser; by patient confirmation on the monitoring client; and/or by a pill-viewing camera.

The pill dispenser may include a microphone and a speaker. The monitoring client may transmit audio data played as sound via the speaker and the monitoring client receives audio from the microphone. For example, the monitoring client may be a Smartphone that can establish two-way audio communications between the monitoring client and Smartphone. The pill dispenser and the monitoring client may be configured for two-way audio and visual communications therebetween, e.g., via video conferencing. The monitoring client may prompt a user for a compliance determination (e.g., a pop-up dialog may ask "Did you take your pill?" with selectable yes and no buttons). The compliance determination may be logged by at least one of the pill dispenser and the monitoring client.

The system includes a monitoring client, a pharmacy computer, a pill-loading robot, a pill dispenser, and a data download device. The monitoring client is configured to communicate a prescription order via a user interface. The pharmacy computer is in operative communication with the monitoring client to receive the prescription order.

The pill-loading robot is in operative communication with the pharmacy computer to receive the prescription. The pill dispenser has a memory and is configured to house one or more pills corresponding to the prescription order. The pill-loading robot is configured to insert the one or more pills into the pill dispenser in accordance with the prescription. The data download device is in operative communication with the pharmacy computer to receive the prescription order. The data download device is configured to download the prescription order from the pharmacy computer into the memory of the pill dispenser. The data download device may be operatively coupled to the pill-loading robot such that the pill-loading robot instructs the data download device to download the prescription order into the pill dispenser.

In yet another aspect of the present disclosure, a system for preparing a pill dispenser includes a monitoring client, a pharmacy computer, a compounding robot, a pill dispenser, and a data download device. The monitoring client is configured to communicate a prescription order via a user interface. The pharmacy computer is in operative communication with the monitoring client to receive the prescription order. The compounding robot is configured to prepare the prescription into one or more pills corresponding to the prescription order. The compounding robot may receive the prescription order from the pharmacy computer. The pill dispenser receives the one or more pills corresponding to the prescription order. The data download device is configured to download the prescription order into a memory of the pill dispenser. The data download device may receive the prescription order from the compounding robot and/or the pharmacy computer. The compounding robot may load the one or more pills into the pill dispenser. In some embodiments, the data download device is operatively coupled to the compounding robot such that the compounding robot instructs the data download device to download the prescription order into the pill dispenser.

In yet another aspect of the present disclosure, a method for dispensing a pill includes: instructing a pill-dispensing mechanism to dispense a pill; instructing a first pill-viewing camera to capture a first image of the pill; determining a presence of the pill within the first image; instructing the first pill-viewing camera to capture a second image; determining an absence of the pill within the second image; instructing an identifying camera to capture a third image; and identifying a user using the third image.

In another aspect of the present disclosure, a pill dispenser includes a body and a camera. The body has a plurality of recesses each adapted to receive a pill container. The camera is positioned to capture an image of a pill container disposed within a recess of the plurality of recesses. A processor may be coupled to the camera to read a label disposed on an inserted pill container inserted into a recess of the plurality of recesses. The processor may determine one or more parameters including one or more of: a dosage value, a refill date, a refill time, characters on the label, a time of insertion of the pill container, a date of insertion of the pill container, a number of pills in the pill container, and/or a date of filling a prescription using an image of a label on a inserted pill container inserted into a recess of the plurality of recesses. The parameter is communicated to a monitoring client.

The pill dispenser may have another camera disposed on a periphery of the body. The pill dispenser may have a touch screen configured to provide a user interface (e.g., disposed within the center of the plurality of recesses as viewed from the top).

In yet another aspect of the present disclosure, a pill dispenser includes a housing, a pill-dispensing mechanism, a pill-dispensing instructor, a receptacle, a first pill-viewing camera, an identifying camera, and an image analysis unit.

The housing defines an opening. The pill-dispensing mechanism is disposed within the housing and is operatively coupled to the opening. The pill-dispensing instructor is arranged to instruct the pill-dispensing mechanism to dispense a pill. The receptacle is operatively coupled to the housing. The first pill-viewing camera is positioned to capture an image of the receptacle and is arranged to capture a first image and a second image. The identifying camera is positioned to capture an image of an area adjacent to the housing and is arranged to capture a third image. The image analysis unit is arranged to determine whether a pill is present within the first image and whether a pill is present within the second image.

The pill dispenser may further comprise a compliance determining unit arranged to determine that compliance has occurred if the first image includes an image of the pill and the second image does not include an image of the pill.

The identifying camera may be arranged to capture the third image a predetermined amount of time after the pill-dispensing instructor instructs the pill-dispensing mechanism to dispense a pill.

The pill dispenser may further comprise a button operatively coupled to the housing. The pill dispenser may be configured such that: (1) when the button is pressed, the pill-dispensing instructor instructs the pill-dispenser to dispense a pill; (2) when the button is pressed, the identifying camera captures the third image; and/or (3) when the button is pressed, the identifying camera captures a plurality of images including the third image in accordance with a predetermined schedule.

The image analysis unit may be arranged to identify whether at least one face is present in an image captured by the identifying camera. The pill dispenser may be configured such that when the button is pressed, the identifying camera captures a series of images until the image analysis unit identifies the presence of at least one face in a captured image of the series of captured images.

The pill dispenser may further comprise a storage medium. And, the pill dispenser may be arranged to store the third image in the storage medium and encrypt the third image within the storage medium. The stored third image may be encrypted using a public key of a pair of asymmetrical encryption keys. The pill dispenser may further comprise a transmitter arranged to transmit the encrypted third image to a server.

The image analysis unit may be arranged to determine whether a face within the third image is an authorized user, and the pill dispenser further comprises a transmitter which is arranged to communicate the third image to a server with an indication of whether the face within the third image is authorized.

In yet another embodiment of the present disclosure, a pill dispenser includes a housing, a pill-dispensing mechanism, a pill viewing location, first and second pill-viewing cameras, one or more processors, and a storage medium. The housing defines an opening. The pill-dispensing mechanism is disposed within the housing and is configured to dispense a pill. The pill viewing location is operatively coupled to the pill-dispensing mechanism. The first pill-viewing camera is positioned to capture an image of the pill viewing location. The second pill-viewing camera is positioned to capture an image of the pill through a transparent window associated with the pill viewing location. The one or more processors are in operative communication with the pill-dispensing mechanism and the first pill-viewing camera. The storage medium for storing processor-executable instructions is configured for execution by the one or more processors to cause the one or more processors to: instruct the pill-dispensing mechanism to dispense a pill to the pill viewing area; instruct the first pill-viewing camera to capture a first image of the pill; instruct the second pill-viewing camera to capture a second image of the pill; and identify the pill using the first and second images.

The one or more processors may identify the pill using one or more of a color of the pill, a shape of the pill, characters on the pill, and a plurality of colors of the pill as determined using the first and fourth images.

The pill viewing area may be external to the housing or internal to the housing. The instructions may cause the one or more processors to dispense the pill to a pill holding area outside of the housing.

The pill dispenser may include a scale. The one or more processors may be in operative communication with the scale to receive a weight therefrom. The instructions may cause the one or more processors to identify the pill based upon, at least in part, an estimated weight of the pill using the scale. The weight of the pill may be determined by subtracting an estimated weight of the pill holder from the weight received by the scale.

The instructions may cause the one or more processors to not dispense the pill unless the identity of the pill is determined to be appropriate based on information from one or more of an electronic medical record, a drug error reduction system, and/or a monitoring client.

In yet another embodiment of the present disclosure, a pill dispenser includes a housing, a pill viewing location, a pill-dispensing mechanism, a door mechanism, a pill-viewing camera, one or more processors, and a storage medium. The housing defines an opening. The pill viewing location is disposed within the housing and is operatively coupled to the opening. The pill-dispensing mechanism is disposed within the housing and is configured to dispense a pill into the pill viewing location. The door mechanism is associated with the pill viewing location and is configured to hold the pill within the pill viewing location and dispense the pill through the opening. The pill-viewing camera is positioned to capture an image of the pill viewing location. The one or more processors are in operative communication with the pill-dispensing mechanism, the pill-viewing camera, and the door mechanism. The storage medium for storing processor-executable instructions is configured for execution by the one or more processors to cause the one or more processors to: instruct the pill-dispensing mechanism to dispense a pill to the pill viewing area; instruct the pill-viewing camera to capture an image of the pill; verify the pill using the image; and instruct the door mechanism to dispense the pill from the pill viewing location through the opening after the pill is verified using the image.

BRIEF DESCRIPTION OF THE DRAWINGS

These and other aspects will become more apparent from the following detailed description of the various embodiments of the present disclosure with reference to the drawings wherein:

FIG. 9 shows a pill dispenser having a dispensing mechanism that dispenses one or more cartridges in accordance with an embodiment of the present disclosure;

FIG. 10 shows pill cartridges of FIG. 9 in accordance with an embodiment of the present disclosure;

DETAILED DESCRIPTION

Figure 1:
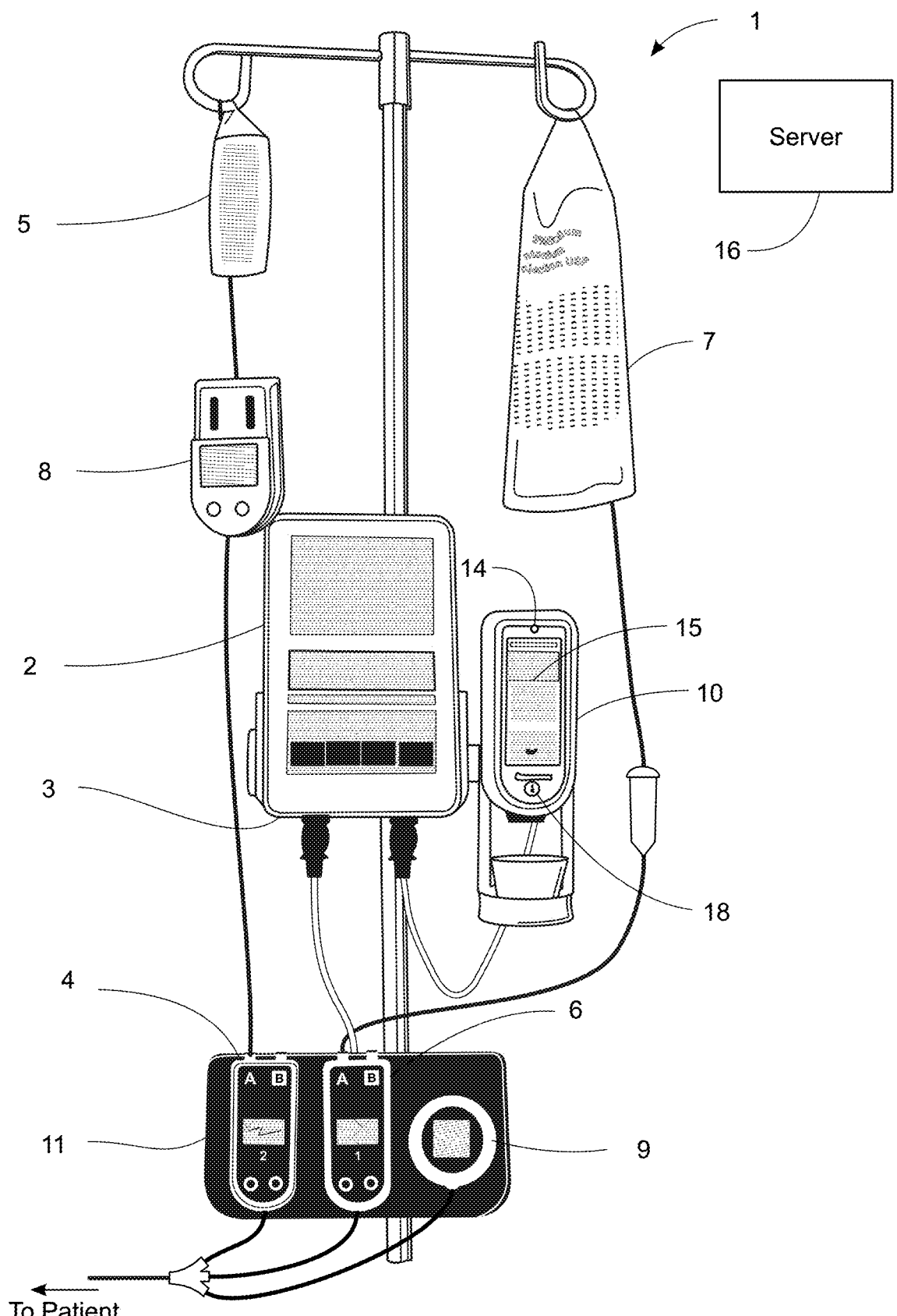
FIG. 1 shows an illustration of an electronic patient-care system having a pill dispenser in accordance with an embodiment of the present disclosure.

FIG. 1 shows an exemplary arrangement of a system 1 for electronic patient care in accordance with an embodiment of the present disclosure. The system 1 includes a monitoring client 2 (e.g., Smartphone, IPod, Ipad, Blackberry-OS based phone or device, Android-based phone or device, tablet computer, laptop, PDA, an audio/visual device such a television with an adapter having a processor and communications capability, etc.) that is linked to a number of patient-care devices via docks 3 and 11, including an infusion pump 4 connected to and delivering from a smaller bag of liquid 5, an infusion pump 6 connected to and delivering from a larger bag of liquid 7, a drip-detection device 8 connected to tubing from the smaller bag 5, and a microinfusion pump 9. System 1 also includes a pill dispenser 10 connected wirelessly to the monitoring client 2. In some embodiments, the monitoring client 2 may communicate with these patient-care devices in a wired fashion, as shown in FIG. 1 for the infusion pumps 4 and 6, the microinfusion pump 9 (via docks 3 and 11), and the pill dispenser 10. Additionally or alternatively, the monitoring client 2 may communicate wirelessly with patient-care devices, as suggested by the absence of a wired connection between the drip-detection device 8 and the monitoring client 2.

For example, the communications between the pill dispenser 10 and the monitoring client 1 may be via a USB cable coupled between the dock 3 and the pill dispenser 10. Other wired or wireless communications may be made between the monitoring client 2 and the pill dispenser 10, including parallel or serial communications, WiFi, Zigbee, mesh networking, Bluetooth (e.g., via pairing), FireWire, fiber optics, or using any known communication protocol, method or technology. For example, the pill dispenser 10 and the monitoring client 2 may communicate over a USB cable, and in the event that communication via the USB cable is unavailable between the monitoring client 2 and the pill dispenser 10, the pill dispenser 10 and the monitoring client 2 may communicate wirelessly. In some embodiments of the present disclosure, the pill dispenser 10 may have a communication module attached thereto enabling the pill dispenser 10 to communicate using a protocol functionality provided by the communication module and/or several communication modules may be connected together and then connected to the pill dispenser enabling the pill dispenser 10 to communicate via the several communication modules.

In some embodiments, a wired connection between the monitoring client 2 and a patient-care device also affords an opportunity for electrical power to be supplied to the patient-care device from the monitoring client 2. In this exemplary embodiment, the monitoring client 2 may include the electronic circuitry necessary to convert a voltage source to power the patient-care device, e.g., the pill dispenser 10, from either a battery attached to the monitoring client 2 or from an Alternative Current ("AC") line voltage fed into the monitoring client 2 from a power outlet (not shown) in a patient's room. Additionally or alternatively, in some embodiments, the pill dispenser 10 may be electrically coupled to the dock 4 (e.g., via a USB cable) which supplies power to the infusion pumps 4 and 6, to the microinfusion pump 9, and/or to the pill dispenser 10 e.g., from a signal generated from an AC line voltage.

The dock 3 may be configured to receive one or more patient-care devices via a standardized connection mount or, in some cases, via a connection mount individualized for the particular device. For example, infusion pumps 4 and 6 may be mounted to the dock 3 via a similar connection mount, whereas the microinfusion pump 9, for example, may be mounted to the dock 3 via a connection mount configured for the particular dimensions of the microinfusion pump's 9 housing. In some embodiments, the pill dispenser 10 is mountable to the dock 4.

In an embodiment, the monitoring client 2 is capable of receiving information about each patient-care device with which it is linked either directly from the device itself or via a docking station, such as, for example, the pill dispenser 10 may supply information stored therein to the dock 3 using a wired or wireless connection, which is then relayed to the monitoring client 2. The docks 3 or 4 may be configured to electronically identify the particular patient-care device being mounted on the docking station and to transmit this identifying information to the monitoring client 2, either wirelessly or through a wired connection. Additionally or alternatively, wireless patient-care devices may transmit the identifying information wirelessly to the monitoring client 2, e.g., during a discovery protocol.

For example, the pill dispenser 10 may be preprogrammed with treatment information, such as a pill dispensing schedule, a pill to be dispensed, the type and number of pills contained therein, etc., that is transmitted to the monitoring client 2. Additionally or alternatively, other information from the pill dispenser 10 may be communicated to the monitoring client 2, such as a list of authorized users or caregivers and their associated authentication information, location information, information from a scanner of the pill dispenser such as barcodes scanned by a camera 14 of the pill dispenser 10, RFID data from an RFID interrogator of the pill dispenser 10, microphone data, sensor data as described herein (e.g., see FIG. 3), or information related to the operation and control of the pill dispenser 10. Additionally or alternatively, logs and/or diagnostic information may be communicated from the pill dispenser 10 to the monitoring client 2.

In some embodiments, the pill dispenser 10 may be programmable to allow for continued operation at a predetermined pill dispensing schedule should communications fail between the monitoring client 2 and the pill dispenser 10 because of a malfunction in the monitoring client 2, in the communications channel between the monitoring client 2 and the pill dispenser 10, or in the pill dispenser 10 itself. In some embodiments, this independent option is enabled when the medication being dispensed is pre-designated for not being suspended or held in the event of a malfunction in other parts of the system. In some embodiments, the pill dispenser 10 is programmed to operate independently in a fail-safe mode.

The pill dispenser 10 may include one or more (e.g., three) drug cartridges that are inserted therein, which can dispense one or more pills. The pill dispenser 10 can dispense drugs by manually pressing the dispense button 18, automatically at preprogrammed or specified times, or by alerting a caregiver to authorize the dispensing. The pill dispenser 10 can log compliance and can track controlled substances to reduce thefts, e.g., through RFID tags, serial number logging, etc.

In some embodiments, operation of the pill dispenser 10, or errors, alerts or alarms of the pill dispenser 10 may be communicated to the monitoring client 2, either wirelessly or in a wired connection. For example, if a scheduled pill to be dispensed is not being dispensed by the pill dispenser 10 (e.g., because of a mechanical malfunction of the pill dispenser 10) or a patient is being noncompliant: (1) a signal may be transmitted to the monitoring client 2, which may trigger an auditory or visual alarm, display the type of error, or display a reminder to a user to take the pill on a user interface of the monitoring client 2 in response to noncompliance; (2) a user interface of the pill dispenser 10, such as a touch screen 15, may display the type of error that has occurred or a reminder for the user to take the pill in response to noncompliance; (3) a remote user interface, such as at a nurse's station or other remote monitoring location, or a handheld communications device may display the type of error that has occurred or a notification of patient noncompliance; (4) the pill dispenser 10 may trigger an auditory or visual alarm; and/or (5) the pill dispenser 10 may alter the pill dispensing schedule to compensate for the medication not being taken (e.g., by adding "catch-up" doses or as modified remotely by a physician in response to a communicated alarm or noncompliance indication via a remote monitoring client, such as a smart phone).

The alarms, alerts, or reminders may occur simultaneously on several devices or may follow a predetermined schedule. For example, when an error occurs within the pill dispenser 10 and/or a user is not taking a scheduled pill (such as non-compliance): (1) the pill dispenser may alarm, issue an alert, or issue a reminder in response to noncompliance using its internal speaker and an internal vibration motor, (2) next, the monitoring client 2 may alarm, issue an alert, or issue a reminder in response to noncompliance using its internal speaker and an internal vibration motor, and (3) finally, a remote communicator (e.g., a smart phone, blackberry-based phone, Android-based phone, iphone, etc.) may issue an alarm or issue an alert using its internal speaker and an internal vibration motor or may indicate to the user the patient's noncompliance.

The pill dispenser 10 includes a touch screen 15 and a dispense button 18. The touch screen 15 may be detachable and may be used to program treatment regimes, a pill dispensing schedule, or other treatment parameters by an authorized user (in some embodiments, the dispensing schedule is preprogrammed at a pharmacy, such as by a pill-loading robot, a compounding robot or a data download device, or the dispensing schedule is downloaded from the electronic medical records 17 of the server 16 directly or through the monitoring client 2 when authorized, for example).

Figure 2:
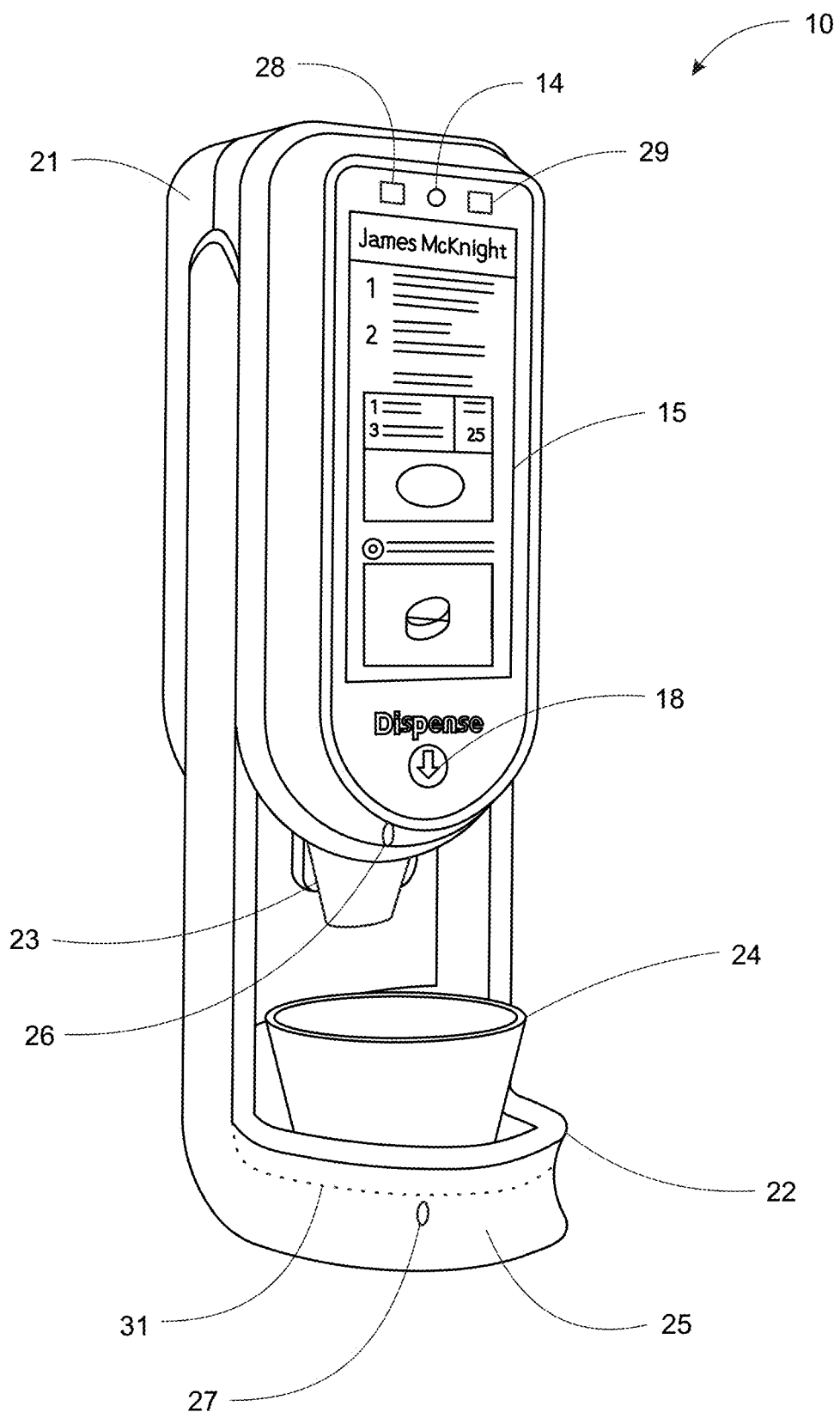
FIG. 2 shows the pill dispenser of FIG. 1 in accordance with an embodiment of the present disclosure.

After a treatment regime (e.g., a pill dispensing schedule) is programmed into the pill dispenser 10, the pill dispenser 10 may query a database 19 (e.g., Electronic Medical Records ("EMR") 17 or Drug Error Reduction System ("DERS") 20 of FIG. 2, or other database) to determine if the treatment regime is safe for the particular patient or for any patient. For example, the pill dispenser 10 may query the EMR database 17 (e.g., via a wireless link, a wired link, WiFi, a cell-phone network, or other communications technology) to determine if the treatment regime from the pill dispenser 10 is safe based upon patient information stored (e.g., age, weight, allergies, condition, etc.) in the EMR's 17 records. Additionally or alternatively, the pill dispenser 10 may query the DERS 20 database of the server 16 (e.g., via a wireless link, wired link, WiFi, cell-phone network, or other communications technology) to determine if the treatment regime from the pill dispenser 10 is safe based upon predetermined safety criteria in the DERS 20 records.

The pills being dispensed and taken by a patient may be monitored by the monitoring client 2 to determine if all the medications being delivered are safe for the patient. For example: (1) the monitoring client 2 may log the medication delivered from the pill dispenser 10 as communicated by the pill dispenser 10 to the monitoring client 2, and (2) the monitoring client 2 may also log the medication being delivered by the infusion pumps 4 and 6, and/or the micro-infusion pump 9. The monitoring client 2 may make a determination from the logged data to determine if the aggregate amounts and types of medication being delivered are safe. For example, the monitoring client 2 may determine if the IV bag 5 is contraindicated with the medication in the pill dispenser 10. Additionally or alternatively, in some embodiments, the monitoring client 2 may monitor the delivery of the liquid in the IV bag 5 and one or more pills delivered by the pill dispenser 10 to determine if the total dose exceeds a predetermined threshold, e.g., the medication in the IV bag 5 and pill dispenser 10 may be the same type or class of drug, and the monitoring client 2 may determine if the drugs are safe when combined as delivered to the patient. The pill dispenser 10 may also communicate with the infusion pumps 4 and 6, and/or the microinfusion pump 9 to make the same determination; In this exemplary embodiment, the pill dispenser 10 may communicate with the devices directly (e.g., wirelessly or through wired communications) or through the monitoring client 2 (e.g., wirelessly or through wired communications) to determine if the intravenously delivered liquid makes the dispending of a pill (e.g., a pill that will be delivered shortly or is scheduled to be delivered as indicated by the pill dispensing schedule) safe for the patient and/or if the intravenously delivered liquid is contraindicated with the pill.

In some embodiments, if the treatment regime is determined to be safe by the pill dispenser 10, the EMR 17, or the DERS 20, a prompt may request user confirmation of the treatment regime. In this exemplary embodiment, after user confirmation, the user (e.g., caregiver, nurse, or other authorized person) may press the dispense button 18.

In some embodiments, if the pill dispenser 10, the EMR 17 and/or the DERS 20 determines that the treatment regime exceeds a first set of criteria, treatment may continue if the user confirms the treatment (e.g., with an additional warning, user passcode, and/or additional authentication or authorization, etc.); in this embodiment, the pill dispenser 10, the EMR 17, or the DERS 20 may prevent the treatment from being delivered if the pill dispenser 10, the EMR 17 and/or the DERS 20 determines that the treatment regime exceeds a second set of criteria, e.g., the treatment is not safe under any circumstances for any patient, for example.

Turning to the drawings, FIG. 2 shows the pill dispenser 10 of FIG. 1 in accordance with an embodiment of the present disclosure. The pill dispenser 10 includes a body 21 and a receptacle 22 coupled to the body. The pill dispenser 10 also includes an identifying camera 14, a touch screen 15, and a dispense button 18.

The touch screen 15 provides a visual interface for a user, such as a patient or caregiver, to interact with the pill dispenser 10. In some embodiments, the touch screen 15 may be removable and/or attachable to the body 21 of the pill dispenser 10.

The identifying camera 14 may be used to authenticate, identify or authorize the user using the touch screen 15. In some embodiments of the present disclosure, the camera 14 may be a panning camera that pans towards an identified face to center the face within images taken by the identifying camera 14. Additionally, a microphone 28 and a speaker 29 may operate together with the touch screen 15 and the identifying camera 14 to facilitate easy user interaction with the pill dispenser 10.

In some embodiments, when the dispenser 10 commences dispensing a pill, such as when button 18 is pressed or when a dispense command is received from monitoring client 2, a pill-dispensing mechanism within the pill dispenser 10 dispenses a pill via a nozzle 23 (a type of opening) out of the body 21. For example, in one specific embodiment: (1) a cartridge includes a plurality of spring-loaded doors each with a flange; (2) an actuator of the pill-dispensing mechanism may engage the flange to open the door to dispense the pill; and/or (3) the actuator may be coupled to a linear actuator that can slide the actuator to a location to open the door. The pill may enter into a cup 24 secured by a cup holder 25 of the receptacle 22. In some embodiments, the cup 24 may contain a transparent window, such as a transparent bottom of the cup.

In other embodiments, when the dispenser 10 commences dispensing a pill, a pill-dispensing mechanism within the pill dispenser 10 dispenses a pill to a shelf within body 21. In one specific embodiment, upon completion of pill verification (e.g., via processor 30 analysis of an image captured of the pill within the shelf), a spring loaded door associated with shelf within the body 21 may open such that the pill may be dispensed via a nozzle 23 (a type of opening) out of the body 21. The door may be controlled by an actuator. The pill may enter then into a cup 24 secured by a cup holder 25 of the receptacle 22. In some embodiments, the shelf within body 21 may contain a transparent window, such as a transparent bottom or floor.

A first pill-identifying camera 26 can capture an image of the pill within the pill viewing location (e.g. a cup 24 or a shelf within the body 21). Additionally or alternatively, a second pill-viewing camera 27 can capture an image of the pill via a transparent window (e.g. transparent bottom of cup 24 or transparent floor of the shelf within body 21). In one specific embodiment, the second pill-viewing camera 27 may be integrated into the receptacle 22.

The pill-viewing cameras 26 and 27 may be used to identify the pill (e.g., to determine that the pill is the correct pill as indicated by a pill dispensing schedule and/or a prescription stored therein) and/or may be used to determined compliance, e.g., to ensure that the patient takes it. In some embodiments of the present disclosure, the identifying camera 14 and/or the microphone 28 may be used to determine compliance.

Figure 3:
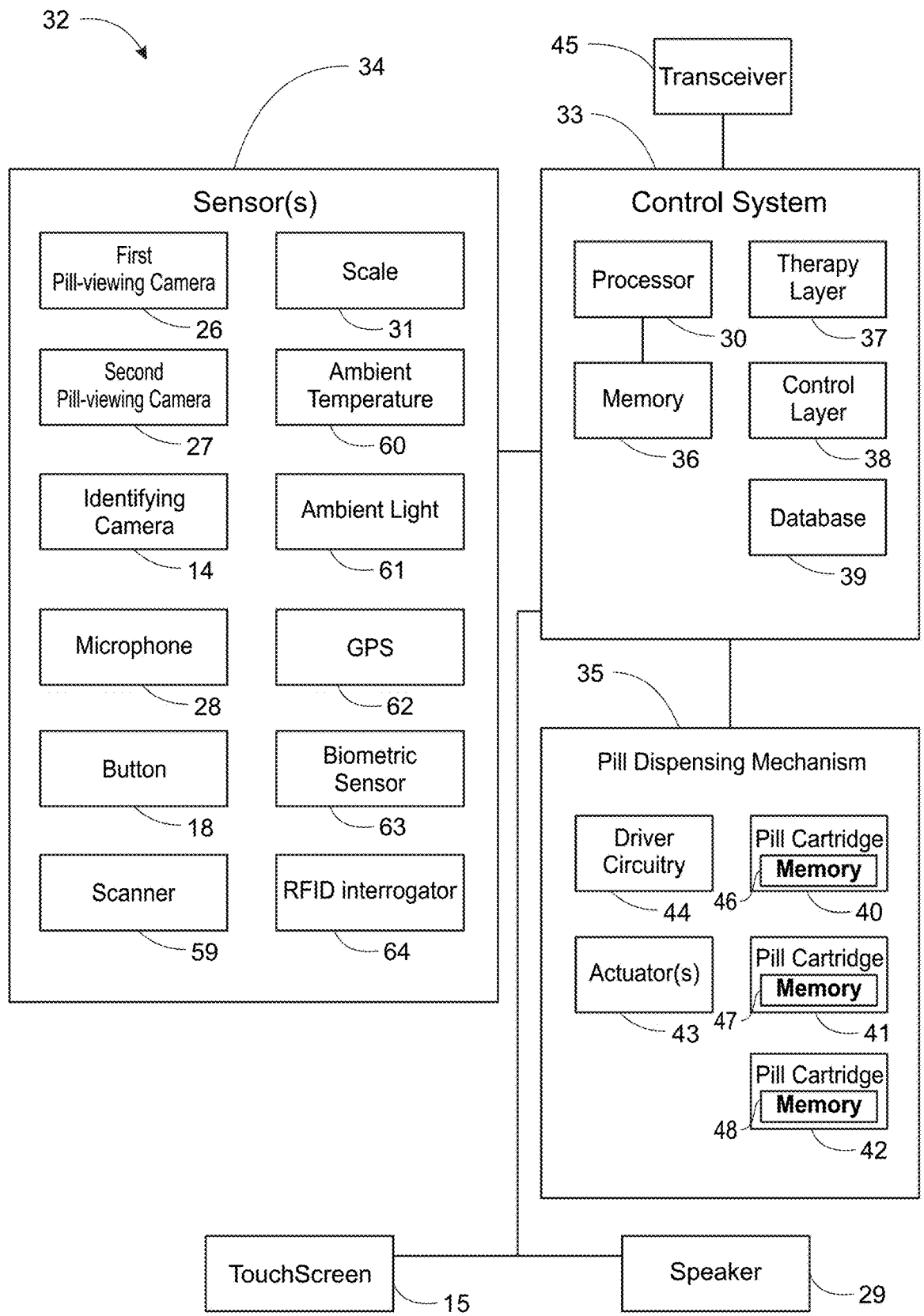
FIG. 3 shows a block diagram of a system for controlling the pill dispenser of FIG. 2 in accordance with an embodiment of the present disclosure.

The pill-viewing cameras 26 and/or 27 may identify the pill by comparing characteristics of the pill with a database 39 (see FIG. 3). For example, a processor 30 (see FIG. 3) may identifying the pill using one or both of the pill-viewing cameras 26 and/or 27 by using a color of the pill, a shape of the pill, characters on the pill (e.g., using optical character recognition), and a plurality of colors of the pill.

The pill dispenser 10 also optionally includes a scale 31. In some embodiments, the scale 31 may be integrated into the receptacle 22. The processor 30 may identify the pill based upon an estimated weight of the pill using the scale 31. The weight of the pill may be estimated by subtracting an estimated weight of the cup 24 disposed within the receptacle 22 from the weight as measured by the scale 31. The weight of the cup 24 may be preprogrammed and/or may be measured prior to dispensing a pill through the nozzle 23 into the cup 24.

In other embodiments, the scale 31 may be integrated with the shelf in the body 21. In such embodiments, the weight of the pill may be estimated by subtracting the weight of the shelf within the body 21 from the weight as measured by the scale 31. The weight of the shelf may be preprogrammed and/or may be measured prior to dispensing a pill onto the shelf.

FIG. 3 shows a block diagram of a system 32 for controlling the pill dispenser 10 of FIG. 2 in accordance with an embodiment of the present disclosure. The system 32 includes a control system 33, a pill-dispensing mechanism 35, and one or more sensors 34. The system 32 also includes output devices, such as the touch screen 15 and the speaker 29 (also see FIG. 2). The system 32 may include one or more communication components for communications, for example the transceiver 45. The control system 33, the pill-dispensing mechanism 35, the one or more sensors 34, the transceiver 45, the touch screen 15, and/or the speaker 29 may be connected together using one or more buses, using wired or wireless serial communications, using wired or wireless parallel communications, single- or multi-channel communications, or using any known communication method, technology, mechanism or interface.

The control system 33 is coupled to the pill-dispensing mechanism 35 to dispense one or more pills. The control system 33 receives various data from the one or more sensors 34 (e.g., the data may be user input) and can output data via the touch screen 15 and/or the speaker 29 to communicate to a user. The control system 33 instructs the pill-dispensing mechanism 35 to dispense one or more pills, e.g., in accordance with a pill dispensing schedule.

The control system 33 includes a processor 30 coupled to a memory 36. The processor 30 and memory 36 may be coupled together through a serial connection, a parallel connection, a memory bus, or other data communications link.

The processor 30 may include one or more cores, may use any instruction set, and/or may use any instruction set architecture or microarchitecture. For example, the processor 30 may have the Von Neumann architecture, the Harvard architecture, may be a microcontroller, may use a MIPS instruction set, a RISC instruction set, and/or a CISC instruction set, etc.

The memory 36 may be any computer-readable medium, processor readable medium, or storage medium. For example, the memory 36 may include one or more memories, such as volatile memory, non-volatile memory, a hard disk, magnetic storage, flash storage, flash ROM, ROM, EEPROM, optical-based memory, memory combining data and instructions, memory having separate memories for data and executable instructions (e.g., a Harvard architecture processor), other non-transitory processor 30 readable medium, the like, or some combination thereof. The memory 36 may be readable by one or more processors 30 and may be implemented by any readable memory device, such as a CD-ROM, a DVD-ROM, or a computer diskette that may have computer readable program code segments stored thereon. The memory 36 may also include a communication or transmission medium, such as, a bus or a communication link, either optical, wired or wireless communication link having program code segments carried thereon as digital or analog data signals that may be sent to the processor 30.

The control system 33 includes a therapy layer 37, a control layer 38, and a database 39 for storing data (e.g., to facilitate the identification of a pill as mentioned herein). The therapy layer 37 and the control layer 38 may be implemented in hardware, software, software in execution on the processor 30, firmware, microcode, assembly, virtualization, bytecode, VHDL, Verilog, a PAL, a PLD, a CPLD, the like, or some combination thereof. For example, the therapy layer 37 and/or the control layer 38 may be stored in the memory 36 as an operative set of processor 30 executable instructions configured for execution on one or more of the processors 30.

The therapy layer 37 may instruct the control layer 38 when and how many pills to dispense from one or more of the pill cartridges 40, 41, and 42. For example, the therapy layer 37 may instruct the control layer 38 to discharge three pills from the pill cartridge 40 and 2 pills from the pill cartridge 41, etc.

The control layer 38 receives a pill dispense command from the therapy layer 37 and controls the position of the one or more actuators 43 to dispense the pills. For example, the control layer 38 may implement a proportional-integral-derivative ("PID") control algorithm having an output to the driver circuitry 44 and feedback from the actuators 43; the set point of the PID control algorithm may be a full or partial rotation of one or more stepper motors (e.g., a type of actuator 43) which corresponds to the dispensing of one pill from the pill cartridge 40, for example.

As previously mentioned, the control system 33 outputs one or more signals to the driver circuit 44 that drives the actuator 43. The driver circuitry 44 may include power MOSFETs, voltage converters, power converters, and/or additional circuitry to receive instructions from the control system 33 and apply one or more sufficient signals to the one or more actuators 43.

The pill dispensing mechanism 35 may includes pill cartridges 40, 41, and 42. The pill cartridges 40, 41 and 42 may each have a respective memory, e.g., memories 46, 47, and 48, respectively. The memories 46, 47, and 48 may include a pill dispensing schedule for a respective pill cartridge, a treatment regime, serial numbers, inventory information related to the pills within the pill cartridges, the number of pills remaining within a cartridge, the number of pills dispensed from the cartridge, encryption keys, patient information, patient serial numbers (e.g., the designated patient for the cartridge), DEA numbers, the name of the pharmacy that filled the prescription, the pharmacy's address or telephone number, the patient's name, the name of the pharmacists that filled the prescription, the license number of the pharmacist that filled the prescription, the expiration date of the pills, the maximum number of pills that may be delivered within a predetermined amount of time, etc.

As previously mentioned, the system 32 includes one or more sensors 34. The sensors 34 optionally includes one or more of: the first pill-viewing camera 26, the second pill-viewing camera 27, the identifying camera 14, the microphone 28, the dispense button 18, a scanner 59, the scale 31, an ambient temperature sensor 60, an ambient light sensor 61, a global positioning system component 62, a biometric sensor 63, and an RFID interrogator 64.

The scanner 59 may be a barcode scanner, a camera (e.g., an additional camera) adapted to read a barcode, an RFID transponder (e.g., another RIFD transponder), and/or a laser barcode scanner.

The ambient temperature sensor 60 may measure the temperature of the air surrounding the pill dispenser 10. The processor 30 is in operative communication with the ambient temperature sensor 60 to receive the temperature measurement therefrom.

The ambient light sensor 61 may measure light around the pill dispenser 10. The processor 30 may use the ambient light sensor 61 to adjust the brightness of the touch screen 15. For example, in very bright condition, the processor 30 may increase the brightness of the touch screen 15.

The global positioning system 62 may determine the geographic position of the pill dispenser 10 and communicate the position to the processor 30.

The biometric identification component 63 may send biometric information to the processor 30. The processor 30 may use the biometric information to authorize and/or authenticate a user, a patient and/or a caregiver. The biometric identification component 63 may be a microphone, a camera, a fingerprint scanner, a hand scanner, an iris scanner, or a retina scanner.

Figure 4:
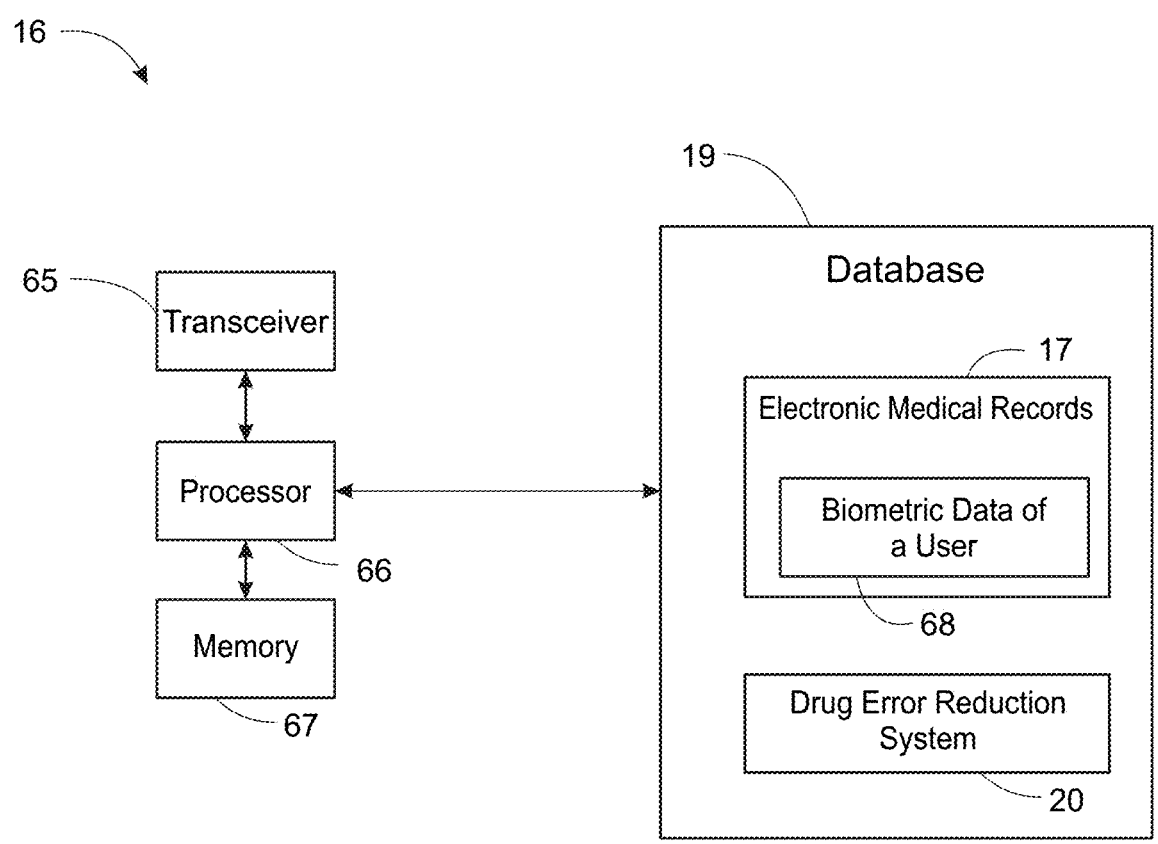
FIG. 4 shows a block diagram of the server of FIG. 1 in accordance with an embodiment of the present disclosure.

FIG. 4 shows a block diagram of the server 16 of FIG. 1 in accordance with an embodiment of the present disclosure.

The server 16 includes a processor 66, a memory 67, a transceiver 65, and a database 19.

The processor 66 is coupled to the memory 67. The memory 67 may include one or more processor-executable instructions configured for execution on the processor 66. The server 16 can receive queries from the pill dispenser 10 or the monitoring client 2 (see FIG. 1) via the transceiver 65.

The processor 66 interacts with the database 19 to respond to the query. The database 19 includes electronic medical records 17 having biometric data 68 of a user or a patient. The database 19 also includes a drug error reduction system 20.

The database 19 may be a Structured Query Language ("SQL") based database, a relational database, a mySQL database, an active database, a cloud database, a data warehouse, a distributed database, an embedded database, an in-memory database, a parallel database, or the like.

The server 16 may interact with the pill dispenser 10 to: (1) authenticate a user, a caregiver, a patient, or other person; (2) track the location of the pill dispenser 10; (3) verify the data, the instructions, the prescription, or other information within the pill dispenser 10; (4) prevent unauthorized use of the pill dispenser 10; (5) disable the pill dispenser 10 in the event of a detected theft or malfunction; (6) upload log data from the pill dispenser 10 to the server 16; (7) upload images taken via the pill dispenser 10 into the server 16; (8) upload compliance data from the pill dispenser 10 into the server 16; (9) communicate alarms, alerts, or reminders from the pill dispenser 10 to the server 16; (10) communicate billing information when a pill is dispensed from the pill dispenser 10 to the server 16; (11) relay information from patient-care devices through the pill dispenser 10 to the server 16; and/or (12) provide secure communications between the pill dispenser 10 and the server 16.

Refer now to FIGS. 1, 2, 3, and 4, for a description of some embodiments of the present disclosure for preparing the pill dispenser 10, verifying the safety of the medications within the pill dispenser 10, dispensing a pill from a pill dispenser, determining compliance, and preventing unauthorized use of the pill dispenser 10; These sections may also be used with the pill dispensers of FIGS. 5-14B or any pill dispenser disclosed herein.

Preparing the Pill Dispenser

A physician, caregiver, or other authorized user may use the monitoring client 2 to remotely send a prescription to a pharmacy that is a prescription for delivering pills using the pill dispenser 10. The pill dispenser 10 may be preloaded at a pharmacy such that the patient can take the pill dispenser 10 home after it is filled.

The pill dispenser 10 may be loaded at the pharmacy manually, using automated technologies, or some combination thereof. For example, the pill cartridges 40, 41, and 42 may be manually or automatically loaded with pills at the pharmacy. Likewise, the pill cartridges 40, 41, and 42 may be manually or automatically loaded into the pill-dispensing mechanism 35 at the pharmacy. In a specific embodiment, the pill cartridges 40, 41, and 42 may be preloaded at the pharmacy such that a pharmacists or a pill-loading robot only needs to load the pill cartridges 40, 41, and 42 into the pill-dispensing mechanism 35 (e.g., automatically or manually). Or, in some embodiments, the pill cartridges 40, 41, and 42 are loaded at the pharmacy with pills (e.g., by the pharmacists or pill-loading robot) and then are loaded into the pill-dispensing mechanism 35.

For example, the pharmacy may include one or more computers connected to a network, e.g., the internet, to receive the prescription and queue the prescription within the one or more computers. The pharmacy may use the prescription to compound the drug (e.g., using an automated compounding device coupled to the one or more computers or manually by a pharmacists viewing the queue of the one or more computers)

An automated pill-loading robot may then fill the pill cartridges 40, 41 and 42 in accordance with the prescription received from the pharmacy computer. The pill-loading robot may also fill the pill dispenser 10 with the pill cartridges 40, 41 and 42 in accordance with the prescription. The pill-loading robot may then program the pill dispenser 10 in accordance with the prescription. For example, a treatment regime, such as a pill dispensing schedule, is programmed into the pill dispenser 10 via a data download device. In some embodiments, the pill dispenser 10 may be automatically programmed by the automated compounding device, the pill-loading robot, or a data download device (e.g., the data download device may be integrated with the pill-loading robot and/or the compounding robot in some embodiments). The pill-dispensing schedule, the prescription, treatment information, or other information may be loaded into the memory of the pill dispenser 10. The automated compounding device, the automated pill-loading robot, and the data download device may be integrated together or may be separate and distinct.

The automated compounding device or pill-loading robot may generate a barcode, an RFID tag and/or data. The information within the barcode, the RFID tag, and/or the data may include the treatment regime, the prescription, the pill dispensing schedule, and/or patient information. The automated compounding device or pill-loading robot may: attach the barcode to the pill dispenser 10 or a pill cartridge 40, 41, or 42 of the pill dispenser 10; attach the RFID tag to the pill dispenser 10 or a pill cartridge 40, 41, or 42 of the pill dispenser 10; and/or program an RFID tag or memory within the pill dispenser 10 or a pill cartridge 40, 41, or 42 of the pill dispenser 10 with the information or data. The data or information may be sent to a database 19 (see FIG. 4) that associates the prescription with the pill dispenser 10 or a pill cartridge 40, 41, or 42 of the pill dispenser 10, e.g., using a serial number or other identifying information within the barcode, RFID tag, or memory.

Verifying the Safety of the Medications within the Pill Dispenser

The pill dispenser 10 may have a scanner, e.g., an RFID interrogator that interrogates or a barcode scanner such as one using a camera 14, to determine that the pills within the pill dispenser 10 corresponds to the particular patient (e.g., as determined from a patient's barcode, RFID, or other patient identification). For example, a serial number of the pill dispenser 10 and a serial number of a patient are compared to serial numbers in electronic medical records 17 in a database 19 to determine if they correctly match with an entry of the patient as indicated by the patient's serial number or the patient's name within the electronic medical records 17. The pill dispenser 10 may scan an RFID tag or barcode of a patient to obtain a serial number of the patient using one or more of the scanner 59, the RFID interrogator 64, or the identifying camera 14. In some specific embodiments, the scanner of the pill dispenser 10 may include a copy of the patient's serial number, and the pill dispenser 10 may only operate when it scans an RFID tag or barcode having the proper patient identification encoded therein. In some embodiments, the serial numbers may be encrypted. The pill dispenser 10 may issue an error or alarm if the serial numbers do not match, in some specific embodiments.

Additionally or alternatively, the monitoring client 6 may scan the pill dispenser 10 or a cartridge of the pill dispenser 10 to determine that it contains the correct pills within a pill cartridge, the treatment programmed into the pill dispenser 10 corresponds to the pill dispenser's 10 serial number, and/or the pill dispenser 10 or the cartridges of the pill dispenser 10 are correct for the particular patient (e.g., as determined from a patient's barcode, RFID, or other patient identification). Additionally or alternatively, the monitoring client 6 or pill dispenser 10 may interrogate an electronic medical records database 68 and/or the pharmacy to verify the accuracy of the prescription as located within the memory of the pill dispenser 10 or may download the prescription into the memory (e.g., memory 36) of the pill dispenser 10, e.g., using a serial number encoded in a barcode on the pill dispenser 10.

For example, a scanner of the monitoring client 2 may scan the pill dispenser 10 and download the prescription to program the pill dispenser 10 via a wireless or wired connection. The monitoring client 2 may then scan a barcode or RFID tag of a patient (e.g., using the scanner 59, the RFID interrogator 64, or the identifying camera 14). The monitoring client 2 may interrogate electronic medical records 17 of the server 16 to ensure that the pill dispenser's 10 serial number matches with the pill dispensing schedule and the patient's serial number as indicated by the electronic medical records 17 of the server.

In some embodiments of the present disclosure, the monitoring client 2 communicates with EMR records 17 within the server 16 to verify that the preprogrammed treatment information received from the pill dispenser 10 is safe for an identified patient and/or the preprogrammed treatment information matches the prescribed treatment stored in the EMR records 17 (see FIG. 4).

When a pill is dispensed, the pill dispenser 10 may check the safety of the pill. For example, the pill-viewing cameras 26 and/or 27 may identify the pill by comparing characteristics of the pill using an internal database 39 (see FIG. 3) or by using an external database 19 of a server 16. For example, a processor 30 (see FIG. 3) may be programmed to identify the pill using one or both of the pill-viewing cameras 26 and/or 27 by using a color of the pill, a shape of the pill, characters on the pill (e.g., using optical character recognition), and a plurality of colors of the pill. If the pill dispenser 10 determines that the dispensed pill does not match the pill as indicated within one or more of the memories 46, 47, and/or 48, the pill dispenser 10 may alarm, e.g., by displaying on the touch screen 15 "Do not take this pill!" accompanied by playing an audio recording via the speaker 29 that states "Do not take this pill!" accompanied by a siren, for example.

In some embodiments in which the pill viewing area is within the body 21, if the pill dispenser 10 determines that the dispensed pill does not match the pill as indicated within one or more of the memories 46, 47, and/or 48, the pill dispenser 10 may retain the pill in the body 21. The pill dispenser 10 may play an audio recording via the speaker 29 that states "Medication error. Please contact your medical professional." Alternatively, if the processor determines the pill is of a pre-determined non-critical nature, then the pill dispenser 10 may still dispense the pill into the cup 24 and may play an audio recording via the speaker 29 that states "Do not take this pill. Please discard and confirm," for example.

The functions of the image analysis unit, the pill-dispensing instructor, and the compliance determining unit may all be performed by a single processor, such as the processor 30. Although it has been described that a single processor 30 is configured to perform the functions of the image analysis unit, the pill-dispensing instructor, and the compliance determining unit, it should be appreciated that the functions of the image analysis unit, the pill-dispensing instructor, and the compliance determining unit may be performed by separate processors.

As previously mentioned, the pill dispenser 10 also optionally includes a scale 31. The processor 31 may further identify the pill based upon an estimated weight of the pill using the scale 31. The weight of the pill may be estimated by subtracting an estimated weight of the pill viewing location (e.g. the cup 24 disposed within the receptacle 22 or the shelf disposed within body 21) from the weight as measured by the scale 31. The weight of the pill viewing location may be preprogrammed and/or may be measured prior to dispensing a pill into the pill viewing location.

After dispensing the pill, the pill dispenser 10 may display an image of the pill, e.g., as stored within the database 39, and request user confirmation on the touch screen 15 that the image of the pill matches the pill within the cup 24. If the user indicates that the pill does not match the image, the pill dispenser may alarm to notify the user to not take the pill and send the alarm to the server 16. The pill dispenser 10 may also disable itself, in some specific embodiments.

In some embodiments, the functionality described above may be implemented by the monitoring client 2, e.g., the pill dispenser 10 may be a slave device to the monitoring client 2.

Identifying and Authorizing a User of the Pill Dispenser

The pill dispenser 10 may include various user or patient identification features to ensure that the person dispensing the pills is authorized. For example, in some specific embodiments, the user must be identified and authorized prior to allowing a pill to be dispensed by the pill dispenser 10. The identification and/or authentication of a user may be performed by using the identifying camera 14, using the microphone 28, using the scanner 59, using the global positioning system component 62, using the biometric sensor 63, using the RFID interrogator, using the touch screen 15, or some combination thereof. In some embodiments, the identification, authentication, or authorization of a user described herein may be accompanied with a username and password login using the touch screen 15.

The identifying camera 14 may capture an image of a user in front of the pill dispenser 10 when an indication has been made by the user to dispense a pill, e.g., via the touch screen 15 and/or by pressing the dispense button 18. The identifying camera 14 may also capture an image after the dispense button 18 is pressed, such as after a predetermined time, in accordance with a predetermined schedule, or until an image of a face is captured. The image may be encrypted and communicated to the server 16 for storage of the image, e.g., via the transceiver 45 of the pill dispenser 10 and the transceiver 65 of the server 16.

Additionally or alternatively, a facial recognition algorithm may identify the user by comparing characteristics of the user against an internal database 39 of the pill dispenser 10 and/or by comparing characteristics of the user against biometric data 68 of a user in the electronic medical records 17 of the database 19 of the server 16. The facial recognition algorithm may determine if the identified user is an authorized or unauthorized user. The identity of the user and whether the identified user is an authorized user may be communicated by the pill dispenser 10 to the server 16.

The identifying camera 14 may also decode a barcode within its field of view to determine authorization. For example, a patient, a caregiver, or a user may be required to display a bar-coded badge, for example, to the identifying camera 14 prior to dispensing the pill.

The identifying camera 14 may be a panning camera. The facial recognition algorithm (e.g., running on the processor 30) may identify the presence of a face (with or without identifying the identity of the face) and pan the camera towards to the face, e.g., to center the face within the field of view of the camera, for example.

The microphone 28 of the pill dispenser may be used to determine if the user (e.g., a patient or a caregiver) is authorized to dispense a pill, e.g., as scheduled or as needed. The user may be required to say a password at a prompt of the pill dispenser 10 via the touch screen 15 or the speaker 29.

For example, the processor 30 of the pill dispenser may instruct the speaker to play an audio recording requesting a sequence of words be spoken. The microphone 28 may record sound. The processor 30 may be coupled to the microphone 28 to authenticate a user in accordance with the sound. In another embodiment, the monitoring client 2 records a user using the microphone 28 and authorizes the user using the microphone 28. The monitoring client 2 may communicate a dispense command to the pill dispenser 10 in response to the authorized user and/or may communicate whether or not a user is authorized to dispense a pill; in this exemplary embodiment, the monitoring client 2 may play a series of words via the speaker 29 that the user is requested to recite back to the microphone 28 of the monitoring client 2.

In another embodiment, the pill dispenser 10, via control by the processor 30, may communicate with the server 16 to query the electronic medical records 17. The pill dispenser 10 may download voice data from biometric data of a user 68 from the electronic medical records 17 within the server 16. The voice data may be voice information of one or more authorized users. The pill dispenser 10 may use the biometric data to determine if a recorded voice is an authorized user as indicated by the electronic medical records' 17 entry.

The pill dispenser 10 may use the scanner 59 to determine if a user is an authorized user prior to dispensing a pill. The scanner 59 may be a barcode scanner, a camera adapted to read a barcode (e.g., another camera), an RFID transponder, and a laser barcode scanner. The scanner 59 may scan a card, a wristband or clothing of a user to identify and/or determine if a user is an authorized user.

The pill dispenser 10 also includes the global positioning system component 62 that can determine the location of the pill dispenser 10. The global positioning sensor component 62 may be used to determine the geographic position of the pill dispenser 10, such as the latitude, the longitude, the country, the state, the county, the city, the town, etc. of the pill dispense 10. The processor 30 may use the position as determined from the global positioning system component 62 to determine if the position of the pill dispenser 10 is within a predetermined authorized area. The pill dispenser 10, for example, may only dispense a pill when the pill dispenser 10 is within the predetermined authorized area and/or when the user is using the pill dispenser 10 within the predetermined authorized area. When the pill dispenser 10 is outside of the predetermined authorized area, the pill dispenser 10 may alarm via the speaker 29 and/or may communicate to the server 16 that the pill dispenser 10 is outside of the predetermined authorized area and may also communicate its position to the pill dispenser 10.

In some embodiments, a position of a user may be communicated to the pill dispenser 10. For example, a Smartphone or other device in the possession of the user may communicate its position to the pill dispenser 10, e.g., via the internet. The pill dispenser 10 will only dispense a pill, in some specific embodiments, if the authorized user and the pill dispenser 10 are within a predetermined distance of each other. The pill dispenser 10 may determine its position using the global positioning system component 62 and may determine the position of the user via the communication component, e.g., the transceiver 45.

The pill dispenser 10 may also determine if a user is authorized to dispense a pill by using the biometric sensor 63 (a type of biometric identification component). The biometric sensor 63 may be controlled by and is communication with the processor 30 of the pill dispenser 10.

The pill dispenser 10 may authentication, identify, and/or authorize a user by using biometric data sensed by the biometric sensor 63. The biometric sensor 63 may be a microphone, a camera, a fingerprint scanner, a hand scanner, an iris scanner, and/or a retina scanner. The pill dispenser 10 may query the electronic medical records 17 to download biometric data of one or more authorized users 68 from the database 19 of the server 16. The pill dispenser 10 may determine if the biometric data from the biometric sensor 63 corresponds to a user as indicated by the electronic medical records 17. The biometric data may also indicate whether the user is authorized to dispense a pill or is presently authorized to dispense a pill e.g., some users may be authorized only during certain periods of times.

The pill dispenser 10 may also use the RFID interrogator 64 to determine if a user is authorized to dispense a pill. For example, the database 39 of the pill dispenser 39 may store a list of numbers associated with authorized users. The RFID interrogator 64 may interrogate an RFID tag of a person (e.g., as found on an ID tag, a credit card size device, access badge, or wristband). If the serial number of the user is listed as being authorized, the pill dispenser 10 may dispense a pill, in some embodiments. Additionally or alternatively, the pill dispenser 10 may download a list of numbers associated with the authorized user from the electronic medical records 17 of the database 19 of the server 16.

In some embodiments, the functionality described above may be implemented by the monitoring client 2, e.g., the pill dispenser 10 may be a slave device to the monitoring client 2 in some specific embodiments Dispensing a Pill As previously mentioned, a pill may be dispensed by the pill dispenser 10 in accordance with a predetermined dispensing schedule, when needed (e.g., when the memory 46 within the pill cartridge 40 designates one or more pills as an as-needed pill), when dispensing the pill does not exceed predetermined safety criteria (e.g., as in the memory 46 or as determined via DERS 20) for the particular patient or for any patient, when a user, caregiver, or patient has been authorized, when the pill dispenser 10 is within an authorized area, when the pill dispenser 10 is within a predetermined distance to a user, and/or when no error conditions or internal flags have been determined by the processor 30 to warrant the prevention of the dispensing of pills. In some embodiments, these features may be implemented by the monitoring 2. For example, the monitoring client 2 may completely control the operation of the pill dispenser 10, in some specific embodiments.

In some embodiments, a pill will only be dispensed when the dispense button 18 is pressed. For example, the pill is dispensed after the patient presses the dispense button 18 and the identifying camera 14 captures an image. The touch screen 15 and/or the speaker 29 may audibly or visually remind a patient to take a pill. The reminder may be a prerecorded voice of a person. For example, the reminder may be a recorded voice of a daughter stating "Please take your pill mother! It's time to take it! I want you to be healthy!" or similar recording. In some embodiments, the monitoring client 2 may perform these reminder functions and may display an image or video of the relative. The pill dispenser 10 may initiate the reminder of the monitoring client 2 (via a digital communication signal) or the monitoring client 2 may initiate the dispensing of the pill while playing the reminder using the touch screen, for example, of the monitoring client 2. In some embodiments, the reminder is initiated if compliance is not determined to have occurred within a predetermined amount of time.

When the pill is dispensed, the pill dispenser 10 and/or the monitoring client 2 may display a graphic illustrating how to take the pill. The graphic may be accompanied by audio; for example, a text-to-speech algorithm may convert text stored therein to speech. Additionally or alternatively, spoken words of the user may also be converted to text and stored within the memory 36 for later retrieval.

After the pill is taken, patient-care parameters may be monitored to determine the efficacy of the pill. For example, blood pressure may be monitored and communicated to the server 16 after a blood pressure pill is dispensed. After the pill is dispensed, a bill may be communicated by the pill dispenser to the server 16 such that a bill may be prepared, e.g., prepared for the patient, an insurance company and/or a third-party.

In some embodiments, the functionality described above may be implemented by the monitoring client 2, e.g., the pill dispenser 10 may be a slave device to the monitoring client 2.

Determining Compliance

After the pill is dispensed, the pill dispenser 10 may determine the compliance of taking the pill. The pill dispenser 10 may determine compliance by using the first pill-viewing camera 26, the second pill-viewing camera 27, the identifying camera 14, or another camera position adjacent to the cup 24.

The pill dispenser 10 may capture a first image using the first pill-viewing camera 26, the second pill-viewing camera 27, the identifying camera 14, or another camera position adjacent to the cup 24 to capture one or more additional images of the pill. The pill dispenser 10 may continue to capture one or more images to determine if/when the pill is removed. In some specific embodiments, the pill dispenser 10 may determine that compliance has occurred if the pill is removed.

In some additional embodiments, the pill dispenser 10 may also require that an authorized user or a particular user be present in the field of view of the identifying camera 14 about when the pill is dispensed and/or when the dispense button 18 is pressed to determine that compliance has occurred.

In some specific embodiments, the pill dispenser 10 may require that an image of the pill and a specific user be present in an image taken by the identifying camera 14 to determine that compliance has occurred. In yet additional embodiments, the pill dispenser 10 may require that the specific user and a bottom of a cup 24 appear in an image taken by the identifying camera 14 to determine that compliance has occurred.

The pill dispenser 10 may instruct the identifying camera 14 to capture one or more images in accordance with a predetermined schedule, e.g., in accordance with a schedule after the dispense button 18 is pressed, or until a face is identified within an image captured by the identifying camera 14. The images captured by the identifying camera 14 may be encrypted and sent to the server 16 for storage.

After dispensing the pill, the pill dispenser 10 may display an image of the pill, e.g., as stored within the database 39, and request user confirmation on the touch screen 15 that the image of the pill matches the pill within the cup 24. After user confirmation, the pill dispenser 10 may prompt the user asking if the user took the pill. If the user confirms that the pill was taken, then pill dispenser 10 may determine that the patient has been compliant. Additionally or alternatively, if the user does not confirm that the pill was taken, the pill dispenser 10 may audibly sound a reminder. In some embodiments, the monitoring client 2 prompts the user to determine compliance.

In some embodiments, the pill dispenser 10 may use different methods of tracking compliance based on the type of pill being dispensed, instructions provided by a medical professional, or selected preferences, which preferences may be set, for example, by the patient for whom the pill is prescribed, by family members, or by others.

In some embodiments, the pill dispenser 10 may automatically dispense pills in accordance with the pill-dispensing schedule. For example, the pill dispenser may dispense a vitamin and sound an audible reminder for the patient to take the vitamin.

The compliance may be logged by the pill dispenser 10. The compliance data and/or the log data may be stored internally within the database 19, may be communicated to the monitoring client 2, and/or may be communicated to the server 16 for storage within the database 19. The log entry may include one or more of voice data of a user used to authenticate the user, an image of the user used to authenticate the user, an image of the pill from the first pill-viewing camera 26, an image of the pill from a second pill-viewing camera 27, a location of the pill-dispensing mechanism, a time stamp, a date stamp, a patient ID from an RFID tag, a nurse ID from another RFID tag, an ambient temperature value, and/or an ambient light value. In some embodiments, the log entry is entered into an RFID tag, such as an RFID tag attached to the patient.

In some embodiments, the monitoring client 2 may be remote from the pill dispenser 10. For example, the monitoring client 2 may be a Smartphone. The monitoring client 2 may display a calendar using compliance data or using data from the log downloaded from the pill dispenser, from the database 19 or as stored therein. The calendar may indicate which days the patient was compliant. For example, the calendar may show blue for compliant days and red for non-compliant days. An authorized user may modify the prescription using the interface of the monitoring client 2, e.g., in response to the non-compliant days. The monitoring client 2 and/or the user of the monitoring client 2 may be authenticated and/or authorized prior to viewing or modifying the pill dispensing schedule using any authentication or authorization mentioned herein, e.g., using a username and a password.

If the pill dispenser 10 and/or the monitoring client 2 have determined that noncompliance has occurred, then one of the pill dispenser 10 and/or the monitoring 2 may initiate two-way communications, e.g., such as a Voip call or a telephone call. For example, the monitoring 2 may be a smart phone of a relative. If the pill dispenser 10 determines that non-compliance has occurred, the monitoring client 2 may prompt the user to call the pill dispenser 10, which initiates a video conference between the pill dispenser 10 and the monitoring client 2.

In yet another specific embodiment, the pill dispenser 10 may dispense a pill and activate its identifying camera 14 for remote viewing. A central viewing center may monitor the identifying camera 14 of the pill dispenser 10. An operator at the central viewing center may determine compliance, such as by watching the patient take the pill and logging the determined compliance. The operator may have the ability to monitor many pill dispensers 10. For example, the central viewing center may be part of a subscription service.

In some embodiments, the monitoring client 2 and/or the pill dispenser 10 may be used to capture images of other pills in the possession of a patient (e.g., pills not in the pill dispenser, but prescribed to the patient). The monitoring client 2, the pill dispenser 10, or the sever 16 may keep track of the pills taken and determine if one or more pills within the pill dispenser 10 may be safely taken with the pills (e.g., the pill dispenser 10 may have its pill-dispensing schedule modified, the dispensing of certain pills may be prohibited, or otherwise a caregiver may be alerted if it is determined that dispensing a pill would be unsafe for a patient in light of other pills taken). In some embodiments, an image of the prescription label may be taken by the pill dispenser and/or the monitoring client 10, or other identification techniques of the prescription may be used (e.g., using a scanner), for the same reasons as described herein.

In some embodiments, the functionality described above may be implemented by the monitoring client 2, e.g., the pill dispenser 10 may be a slave device to the monitoring client 2 in some specific embodiments Preventing Unauthorized Use of the Pill Dispenser When the pill is dispensed from the pill dispenser 10, the pill dispenser 10 and/or the monitoring client 2 may capture one or more images using the identifying camera 14 of a camera of the monitoring client 2, respectively. The images may be taken in accordance with a predetermined schedule or until a face is identified in an image when the dispense button 18 is pressed. The one or more images may be communicated to the server 16 for storage and/or may be stored internally. The images may be communicated to the server 16 to determine if an image of an authorized user is in the image. The pill dispenser 10 and/or the monitoring client 2 may determine if the user is an authorized user and send that determination to the server 16 with or without the images. The images may be encrypted, e.g., using a key of an asymmetrical or a symmetrical encryption scheme. The storage of the images may be used in the event the pill dispenser 10 has been stolen, for example. The pill dispenser 10 and/or the monitoring client 2 may audibly and/or visually alarm if an unauthorized person attempts to use the pill dispenser, e.g., after a predetermined number of attempted logins, for example.

Additionally, any attempt to use the pill dispenser 10 and/or the monitoring client 2 may be logged and stored. For example, the pill dispenser 10 may also determine if a user is authorized to dispense a pill by using the biometric sensor 63. The pill dispenser 10 may deny a person the use of the pill dispenser and may log the biometric information. The biometric information may be communicated to the sever 16 for storage within the database 19 along with the indication of the attempted use.

As mentioned above, the pill dispenser 10 also includes the global positioning system component 62 that can determine the location of the pill dispenser. The global positioning sensor component 62 may be used to determine the geographic position of the pill dispenser 10, such as the latitude, the longitude, the country, the state, the county, the city, the town, etc. of the pill dispenser 10. The processor 30 may use the position as determined from the global positioning system component 62 to determine if the position of the pill dispenser 10 is within a predetermined authorized area. The pill dispenser 10, for example, may only dispense a pill when the pill dispenser 10 is within the predetermined authorized area and/or when the user is using the pill dispenser 10 within the predetermined authorized area. When the pill dispenser 10 is outside of the predetermined authorized area, the pill dispenser 10 may alarm via the speaker 29 and/or may communicate to the server 16 that the pill dispenser is outside of the predetermined authorized area and may also communicate its position to the pill dispenser 10. If it is determined that the pill dispenser 10 is stolen, for example, the global positioning sensor component 62 may be used to assist in locating the pill dispenser 10 by assisting law enforcement. The position of the pill dispenser 10 may be continuously logged by the database 19 to keep track of the pill dispenser 10.

Also as previously mentioned, in some embodiments, a position of a user may be communicated to the pill dispenser 10. For example, a Smartphone or other device in the possession of the user may communicate its position to the pill dispenser 10, e.g., via the internet. The pill dispenser 10 will only dispense a pill, in some specific embodiments, if the authorized user and the pill dispenser 10 are within a predetermined distance of each other. The pill dispenser 10 may determine its position using the global positioning system component 62 and may determine the position of the user via the communication component, e.g., the transceiver 45. If it is determined that the pill dispenser 10 has been stolen using this data, the location data of the user and the location of the pill dispenser 10 may be used to assist law enforcement in locating the pill dispenser 10. The position of the user may be continuously logged by the database 19 to keep track of the location of the user.

If the server 16, the monitoring client 2, or the pill dispenser 10 determines that the pill dispenser 10 has been stolen, the pill dispenser 10 may disable itself and/or a signal may be sent from the server 16 or the monitoring client 2 to the pill dispenser 10 instructing the pill dispenser 10 to disable itself. Authentication and/or encryption keys may be used when communicating the signal. For example, a secure signature may be used.

In some embodiments, the functionality described above may be implemented by the monitoring client 2, e.g., the pill dispenser 10 may be a slave device to the monitoring client 2.

Figure 5:
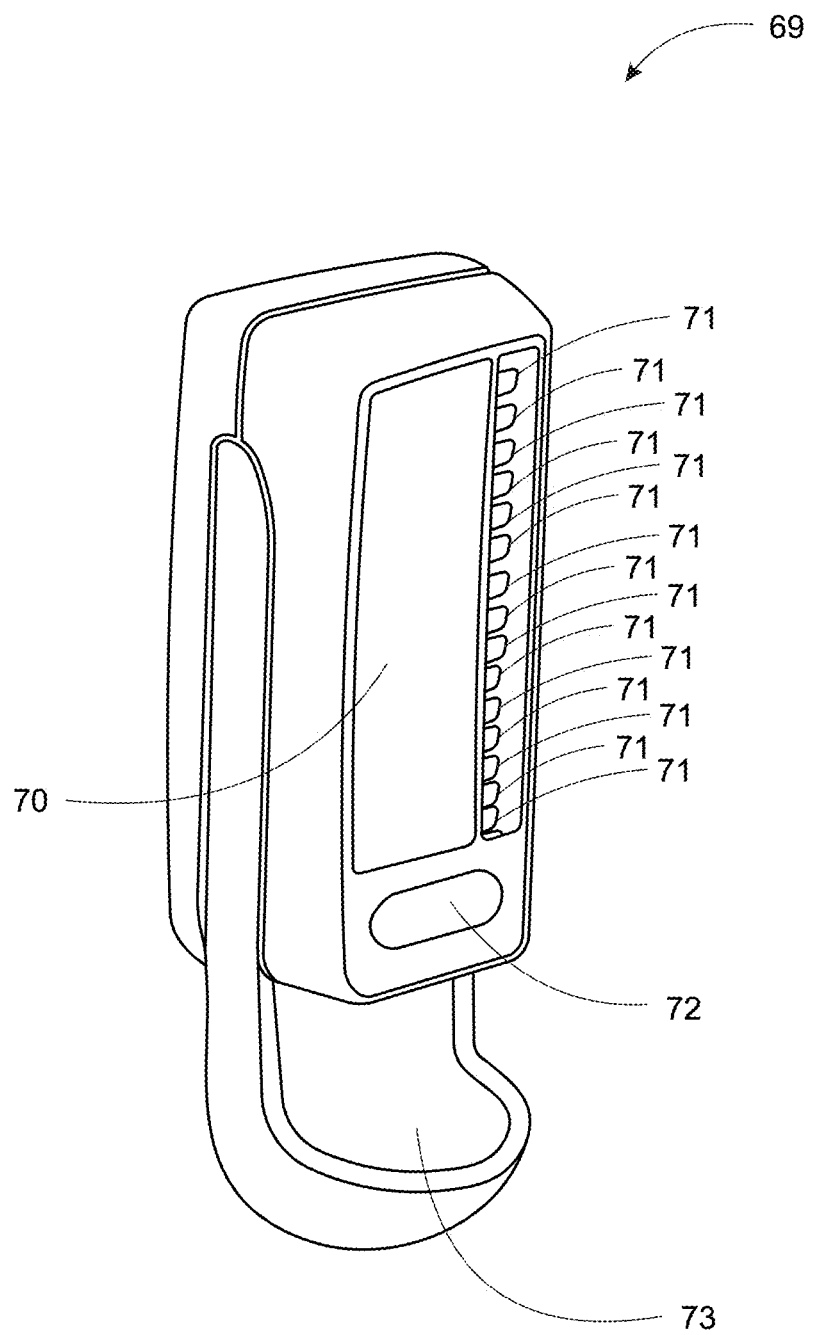
FIG. 5 shows a pill dispenser having a plurality of vertical windows in accordance with an additional embodiment of the present disclosure.

FIG. 5 shows a pill dispenser 69 having a plurality of vertical windows 71 in accordance with an additional embodiment of the present disclosure. The pill dispenser 69 may be used in addition to and/or in place of the pill dispenser 10 with system 1 of FIG. 1, or the pill dispenser 69 may be a standalone device. The pill dispenser 69 may use or include the system 32 of FIG. 3 in some embodiments.

The pill dispenser 70 includes a user interface 70 and a plurality of viewing windows 71. The windows 71 may show the pills within the one or more pill cartridges (40, 41, or 42). A user may press the dispenser button 72 which then dispenses a pill into the receptacle 73.

Figure 6:
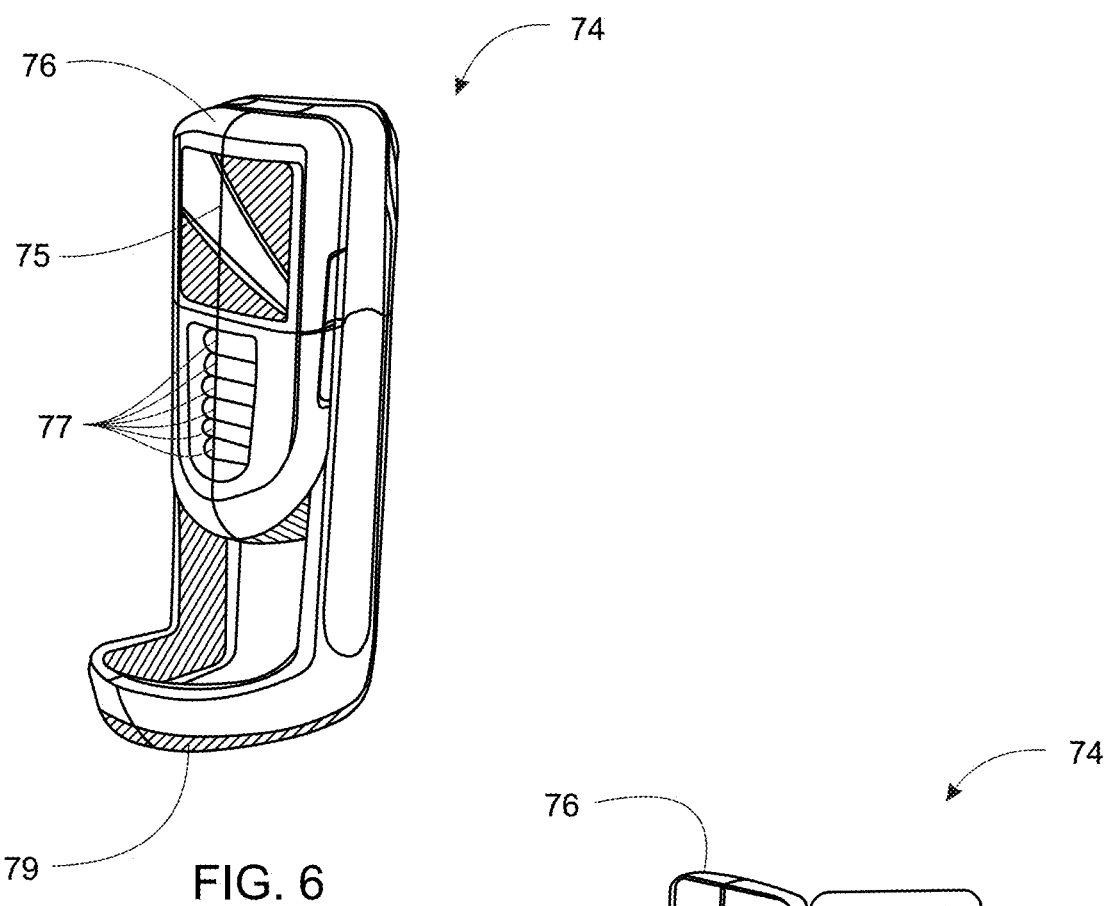
FIGS. 6-7 show a pill dispenser having a plurality of vertical windows below a touch screen in accordance with an additional embodiment of the present disclosure.
Figure 7:
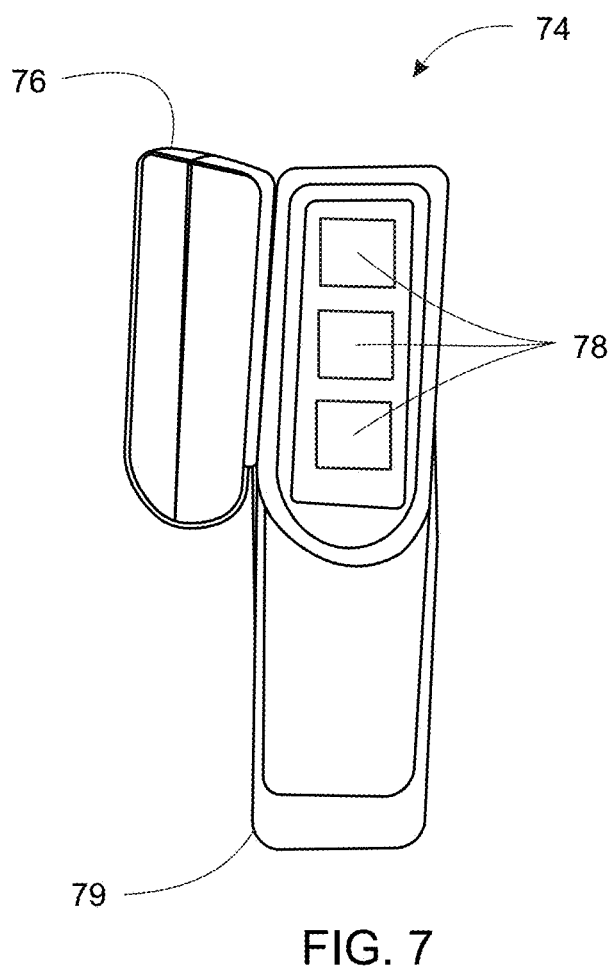

FIGS. 6-7 show a pill dispenser 74 having a plurality of vertical windows 77 below a touch screen 75 in accordance with an additional embodiment of the present disclosure. The pill dispenser 74 may be used in addition to and/or in place of the pill dispenser 10 with system 1 of FIG. 1, or the pill dispenser 69 may be a standalone device. The pill dispenser 74 may use or include the system 32 of FIG. 3, in some embodiments.

The pill dispenser 74 includes a touch screen 75 that is coupled to a door 76 that swings open so that cartridges 78 may be inserted. The touch screen 75 may be used to dispense one or more pills into a receptacle 79. The pill dispenser 74 may also include a plurality of viewing windows 77 that display one or more pills of the one or more pill cartridges 78.

Figure 8:
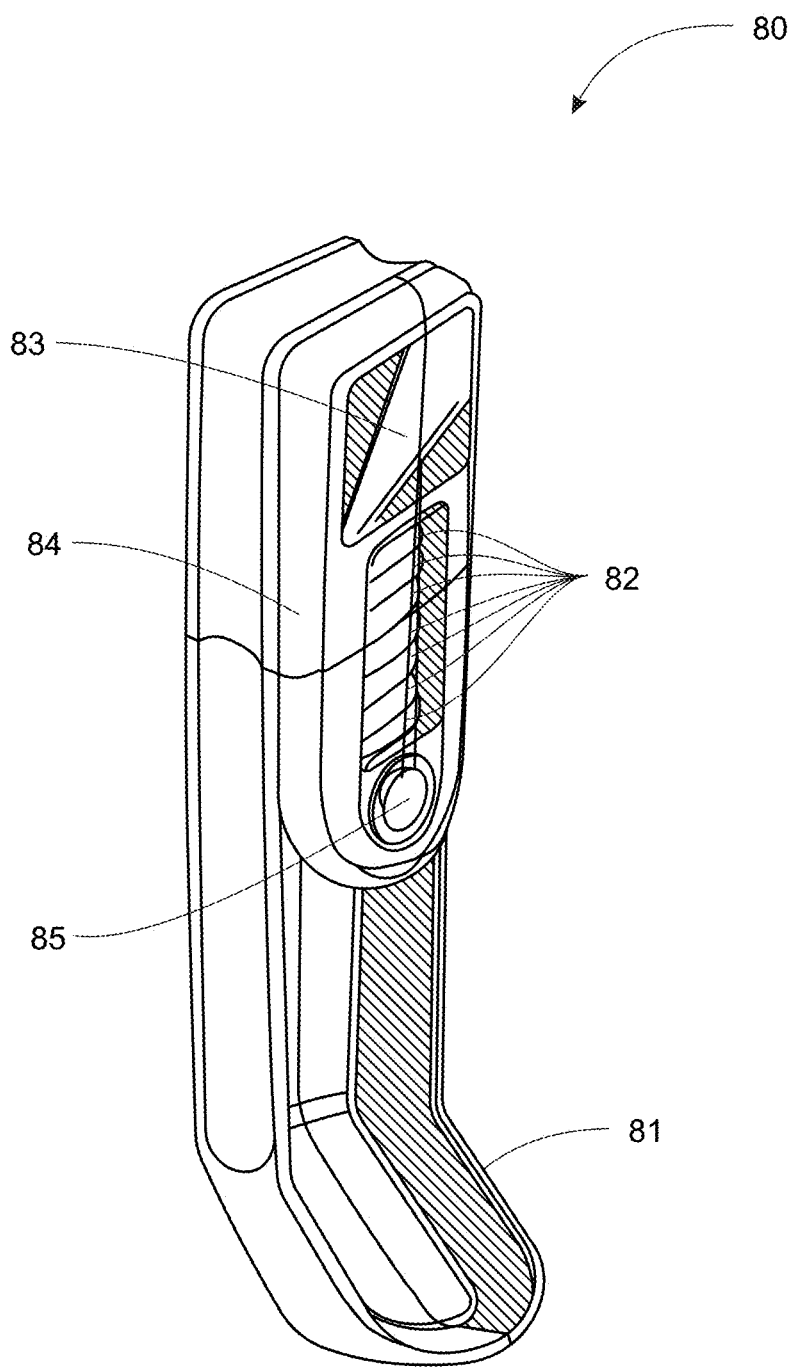
FIG. 8 shows a pill dispenser having a plurality of vertical windows below a touch screen and an elongated receptacle in accordance with an additional embodiment of the present disclosure.

FIG. 8 shows a pill dispenser 80 having a plurality of vertical windows 82 below a touch screen 83 and an elongated receptacle 81 in accordance with an additional embodiment of the present disclosure. The pill dispenser 80 may be used in addition to and/or in place of the pill dispenser 10 with system 1 of FIG. 1, or the pill dispenser 80 may be a standalone device. The pill dispenser 80 may use the system 32, in some embodiments.

The pill dispenser 80 includes a touch screen 83 disposed on a door 84. There is a plurality of viewing windows 82 to view one or more pills. The pills may be dispensed by pressing the dispense button 85. The pills may be dispensed into the receptacle 81.

FIG. 9 shows a pill dispenser 86 having a dispensing mechanism that dispenses one or more cartridges 90 in accordance with an embodiment of the present disclosure. The pill dispenser 86 may be used in addition to and/or in place of the pill dispenser 10 with system 1 of FIG. 1, or the pill dispenser 86 may be a standalone device. The pill dispenser 86 may use or include the system 32 of FIG. 3 in some embodiments.

The pill dispenser 86 includes a touch screen 87 and openings 88 and 89. The pill dispenser 86 may dispense a cartridge 91 out the opening 89 which may then be used and disposed back in to the opening 88. The cartridge 91 may include a snap-on lid coupled to the rest of the cartridge 91 through a living hinge. There may be a camera disposed within the housing of the pill dispenser 86 (e.g., inside, but above, the opening 88 to view the contents of the cartridge 91 when inserted into the opening 88) to determine compliance. FIG. 9 shows a stack of cartridges 90 including the cartridge 91. The pill dispenser 86 may be returned to a pharmacy for refilling. The pill cartridges 90 may be sterilized and/or washed and reused.

Figure 11:
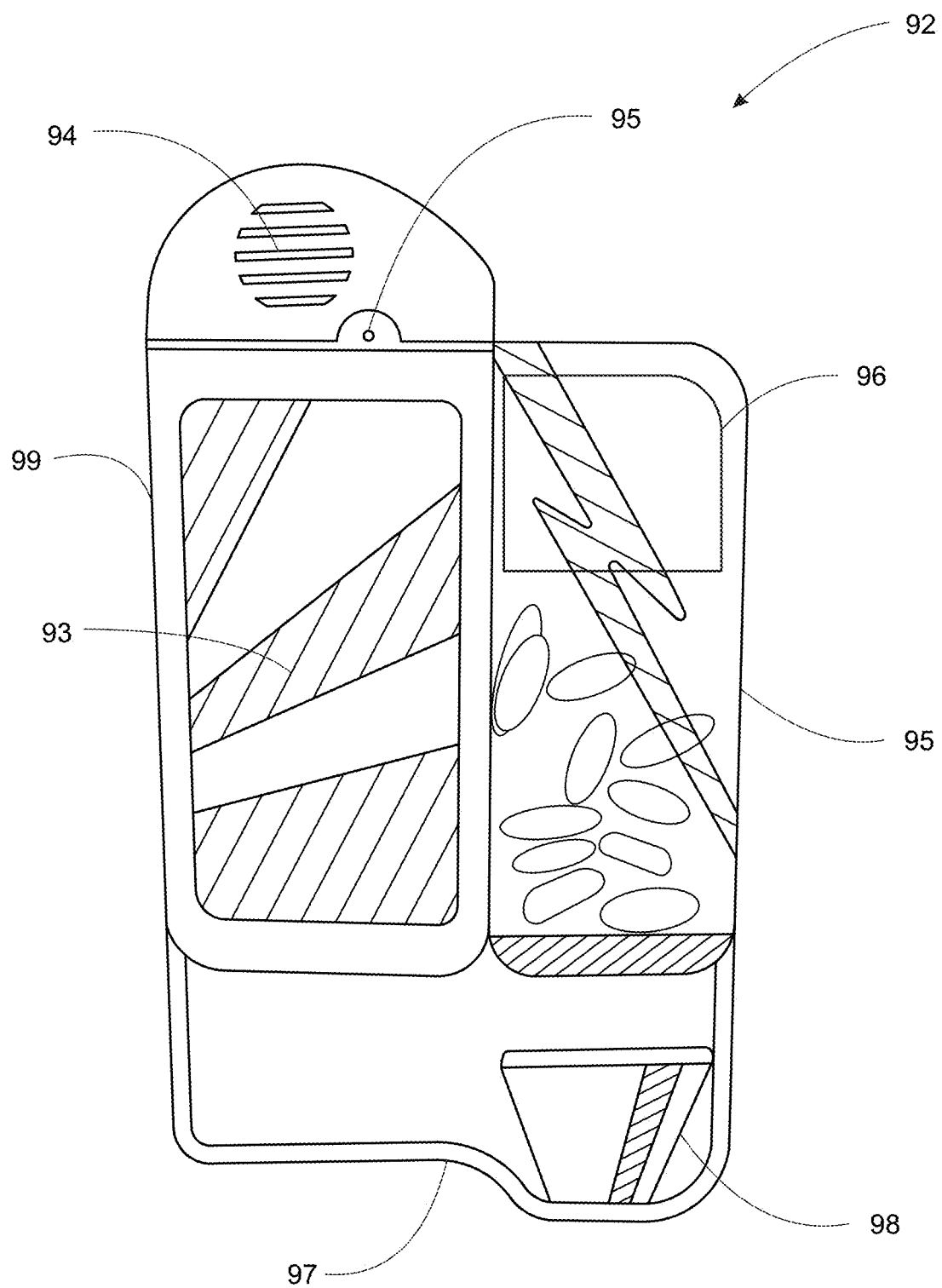
FIG. 11 shows a pill dispenser having a secondary housing along a side thereof in accordance with an embodiment of the present disclosure.

FIG. 11 shows a pill dispenser 92 having a secondary housing 95 along a side thereof in accordance with an embodiment of the present disclosure. The secondary housing 95 may house one or more pill cartridges 96. The secondary housing 95 may be attachable to and/or detachable from the primary housing 99. The pill dispenser 92 may be used in addition to and/or in place of the pill dispenser 10 with system 1 of FIG. 1, or the pill dispenser 92 may be a standalone device. The pill dispenser 92 may use or include the system 32 of FIG. 3, in some embodiments.

The pill dispenser 92 includes a speaker 94, a microphone 95, and a touch screen 93 to dispense a pill. The pills are dispensed from one or more cartridges 96 which are dropped into a cup 98 of a receptacle 97. The pill-dispensing mechanism may be within the primary housing 99, in the secondary housing 95, or may be distributed between of the housings 95 and 99.

Figure 12:
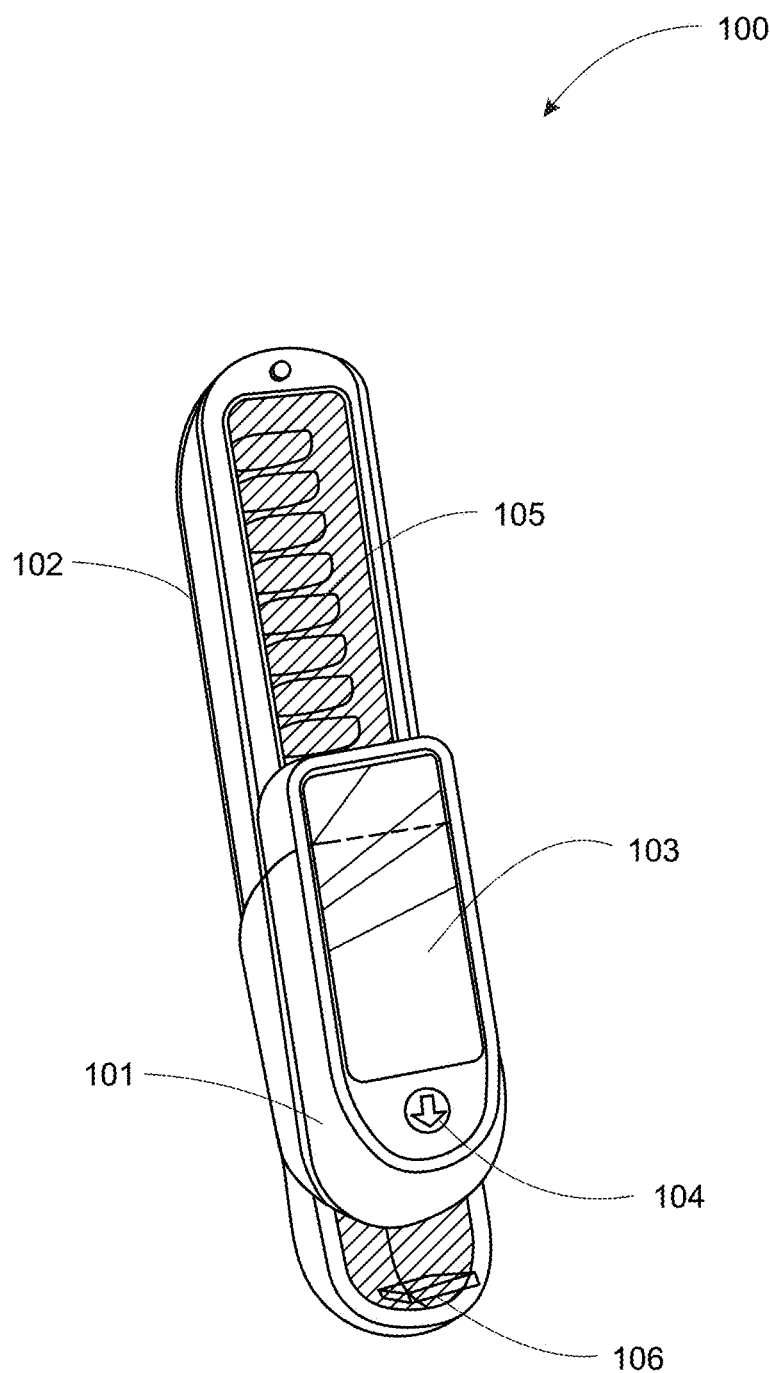
FIG. 12 shows a pill dispenser having a housing coupled to the cartridge and in sliding engagement with the cartridge in accordance with an additional embodiment of the present disclosure.

FIG. 12 shows a pill dispenser 100 having a housing 101 coupled to the cartridge 102 and in sliding engagement with the cartridge 102 in accordance with an embodiment of the present disclosure. The pill dispenser 100 may be used in addition to and/or in place of the pill dispenser 10 with system 1 of FIG. 1, or the pill dispenser 100 may be a standalone device. The pill dispenser 100 may use or include the system 32 of FIG. 3, in some embodiments.

The housing 101 includes a touch screen 103 and a dispense button 104 coupled thereto. The pill cartridge 102 includes a viewing window 105 showing the pills. The housing 101 may slide such that an internal pill-dispensing mechanism may grab the pills stacked vertically and dispense the pills into the receptacle 106.

Figure 13:
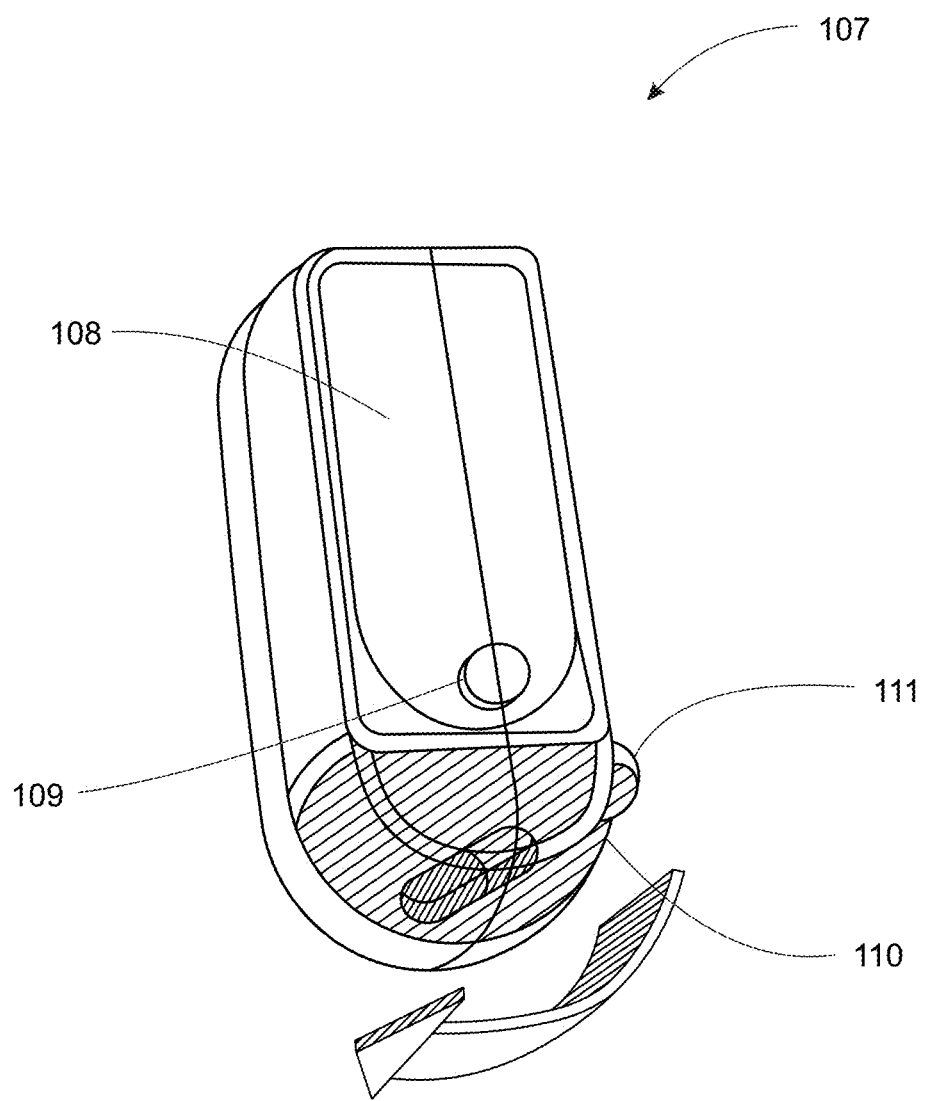
FIG. 13 shows a pill dispenser having a sliding-door for receiving the pill in accordance with an embodiment of the present disclosure.

FIG. 13 shows a pill dispenser 107 having a sliding-door 110 for receiving the pill in accordance with an embodiment of the present disclosure. The pill dispenser 107 may be used in addition to and/or in place of the pill dispenser 10 with system 1 of FIG. 1, or the pill dispenser 107 may be a standalone device. The pill dispenser 107 may use or include the system 32 of FIG. 3, in some embodiments. The pill dispenser 107 includes a touch screen 108 and a dispense button 109. The door 110 can be opened by the knob 111 to dispense a pill.

Figure 14A:
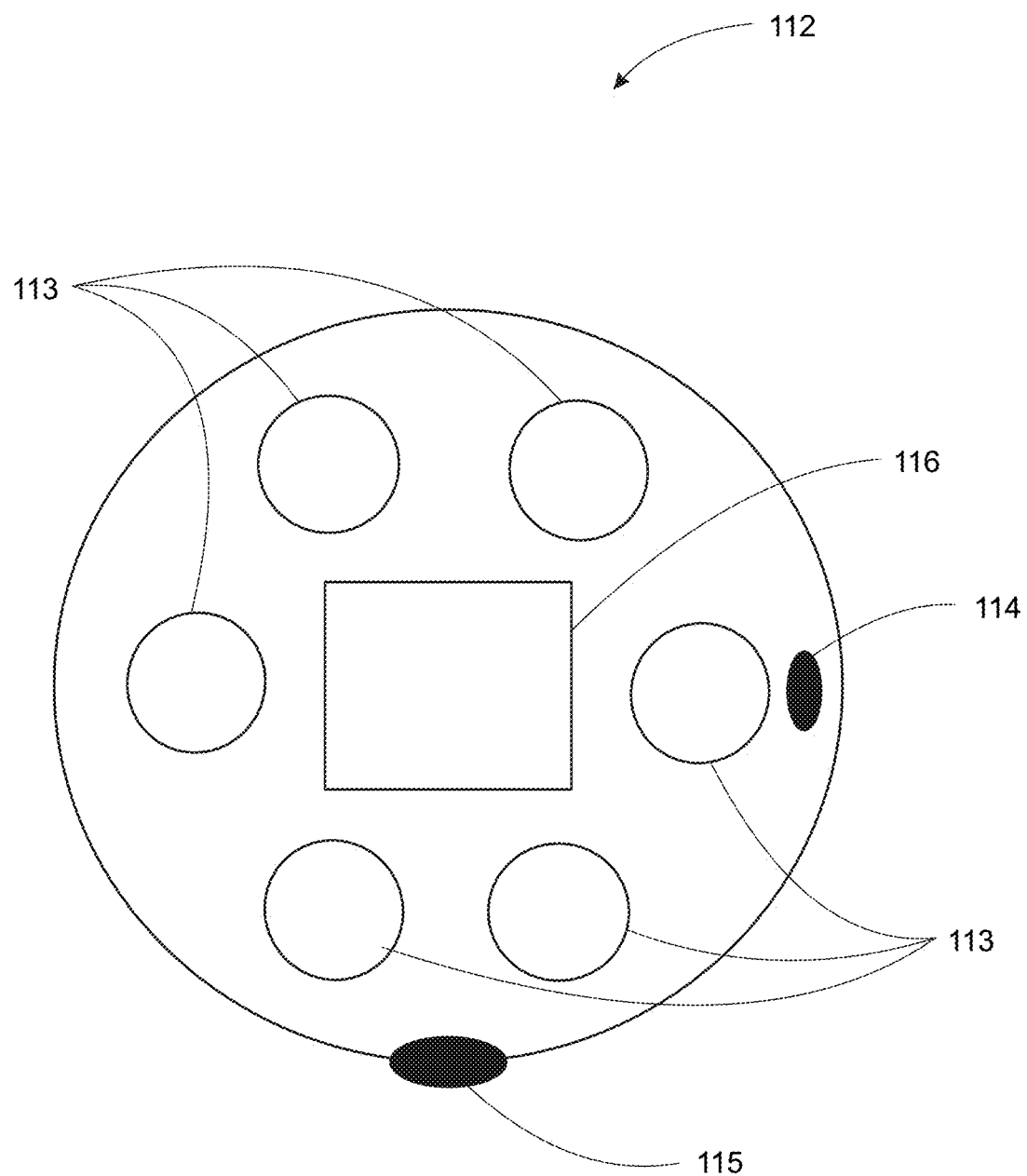
FIGS. 14A-14B show two views of a pill dispenser capable of receiving pill bottles as pill cartridges in accordance with an embodiment of the present disclosure.
Figure 14B:
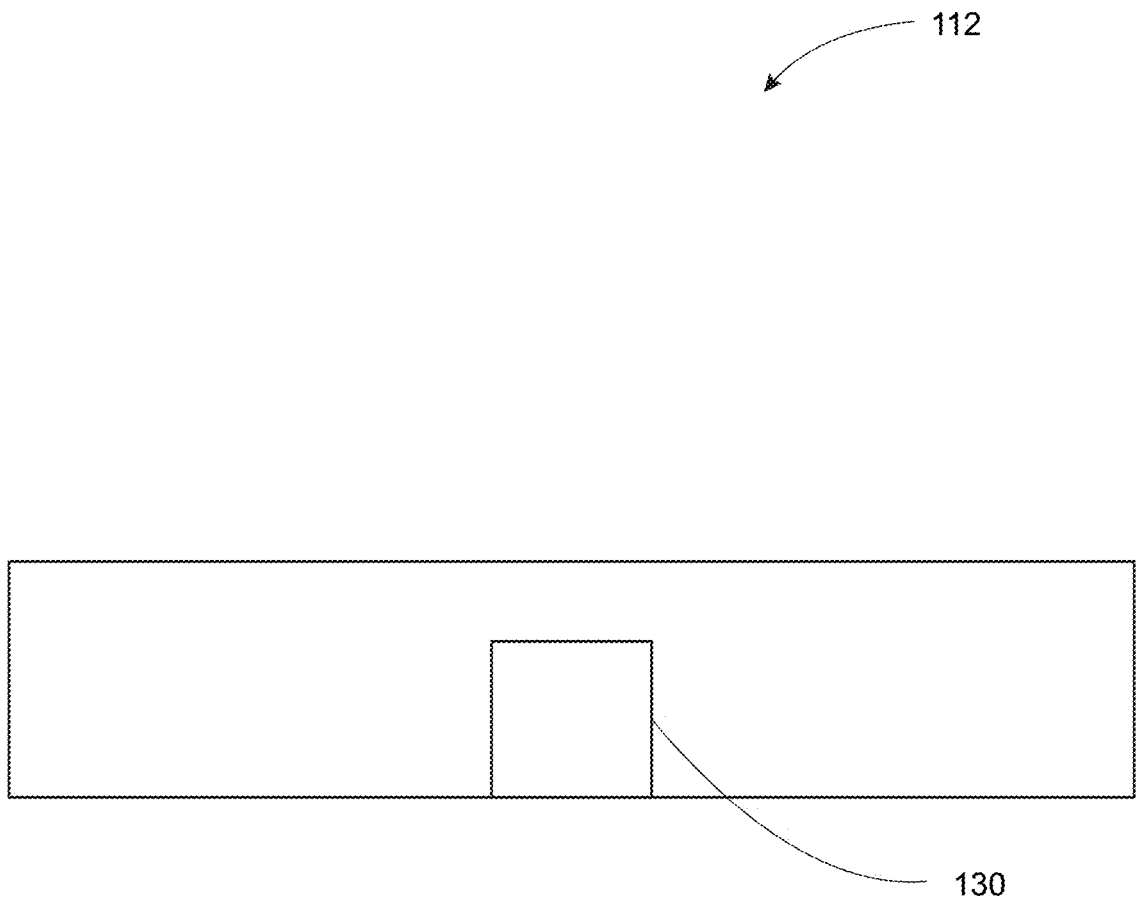

FIGS. 14A-14B show a pill dispenser 112 capable of receiving pill bottles as pill cartridges in accordance with an embodiment of the present disclosure. FIG. 14A shows a top view of the pill dispenser 112, and FIG. 14B shows a side view of the pill dispenser 112. The pill dispenser 112 may be used in addition to and/or in place of the pill dispenser 10 with system 1 of FIG. 1, or the pill dispenser 112 may be a standalone device. The pill dispenser 112 may use or include the system 32 of FIG. 3, in some embodiments.

The pill dispenser 112 includes a plurality of recesses 113 each shaped to receive a pill bottle. The cap of a pill bottle may be taken off and the pill bottle may be placed upside down and inserted into one or the plurality of recesses 113 such that the pills are poured into the recess. The recesses 113, in other embodiments, may include a snap-top door such that pills, e.g., a group for each day of scheduled pills to be taken, may be held within a recess of the plurality of recesses 13. The pills are dispensed out of a trap door 130. The pill-dispensing mechanism may be gumball-type pill dispensing mechanism.

The pill dispenser 112 also includes a touch screen 116, an identifying camera 115, and a pill-bottle identifying camera 114. As mentioned, the pill bottle may be opened and placed up-side down into one of the recesses. A camera 114 can rotate around the pill dispenser 112 to capture one or more images of the labels of the pill bottles including dosage and scheduling information displayed in text or encoded thereon. In some specific embodiments, the rotation may be made by a circular track coupled to stepper motor such that a circular structure having the camera 114 rests on the circular track and the stepper motor rotates the circular structure along the track. The stepper motor may be controlled by the one or more processors 30 within the pill dispenser 112.

The pill-bottle identifying camera 114 may use OCR or information encoded on a barcode to update a pill-dispensing schedule within a memory coupled to a processor 30 therein or to generate a pill-dispensing schedule including a dosage schedule. The pill-bottle identifying camera 114 may read instructions from the label of the pill bottle disposed on the pill dispenser 112. The label information can be compared to a prescription stored in internal memory to determine if an error has occurred and/or when a refill is expected. Additionally, the pill dispenser 112 may access the prescription stored in internal memory to determine if a scheduled pill bottle was actually inserted into a recess 13, which may be logged for compliance tracking; for example, a bottle of 30 pills should be taken every day starting on the first day of a particular month, and if no pills were inserted into a recess 13 on the first day of the particular month, the pill dispenser 112 determines that non-compliance has occurred. The pill-bottle identifying camera 114 may capture: the time of delivery, the number of tablets, the dosage of each pill, the dosage of each scheduled oral taking of one or more pills, when the prescription was filled, a refill time, the pills indicated by the label to be in the bottle, etc. This information may be communicated to a caregiver and/or a patient having a monitoring client 2.

Figure 15:
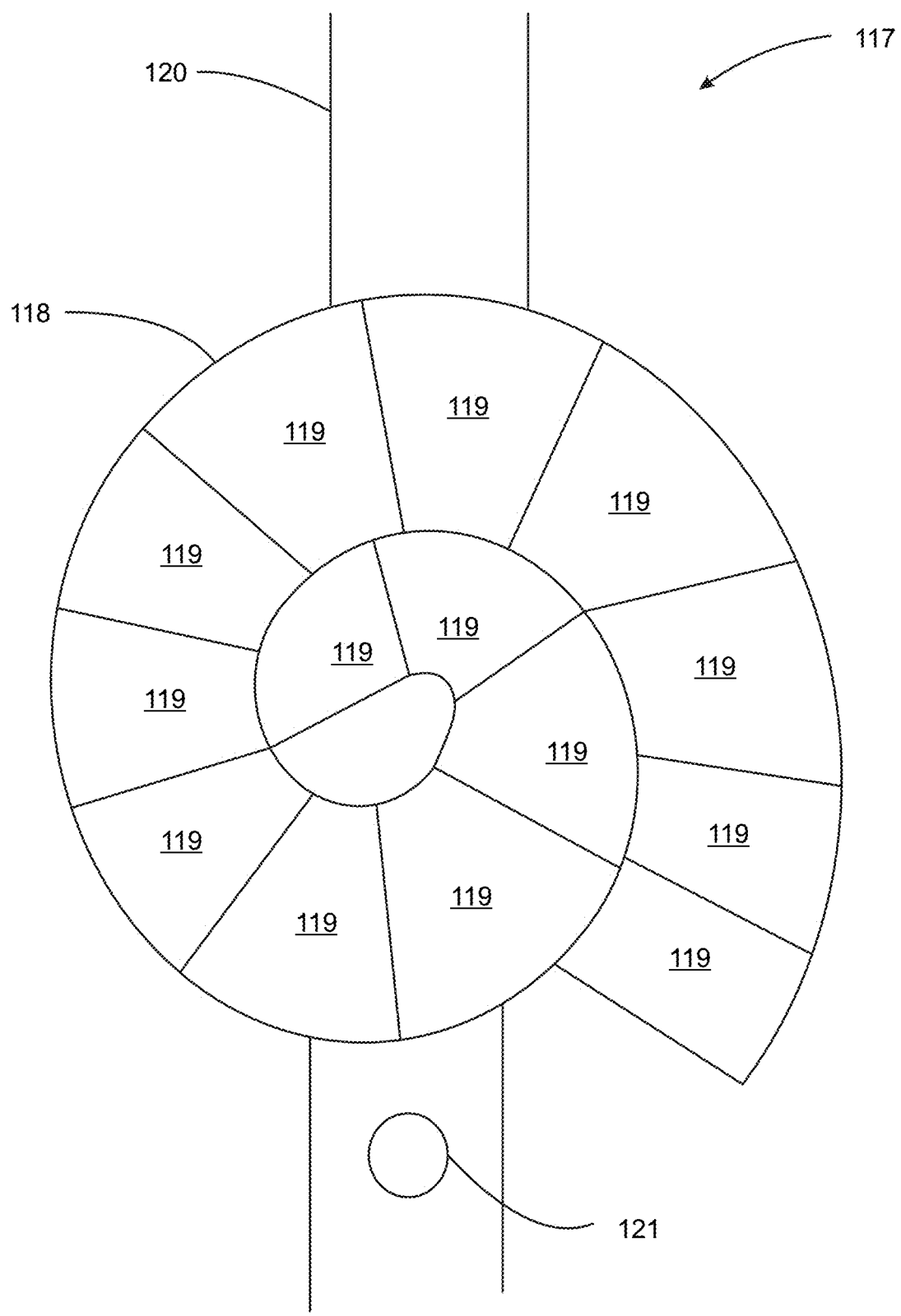
FIG. 15 shows a pill-dispensing mechanism in accordance with an embodiment of the present disclosure.

FIG. 15 shows a pill dispensing mechanism 117 in accordance with an embodiment of the present disclosure. A cartridge 118 includes a plurality of containers 119 to house pills. The cartridge 118 may be rotated by a stepper motor. A sliding member 120 can slide such that a hole 121 moves adjacent to one of the containers 119 to allow the pill to dispenser. The sliding member 120 may be coupled to a linear actuator, e.g., a linear servo.

Figure 16:
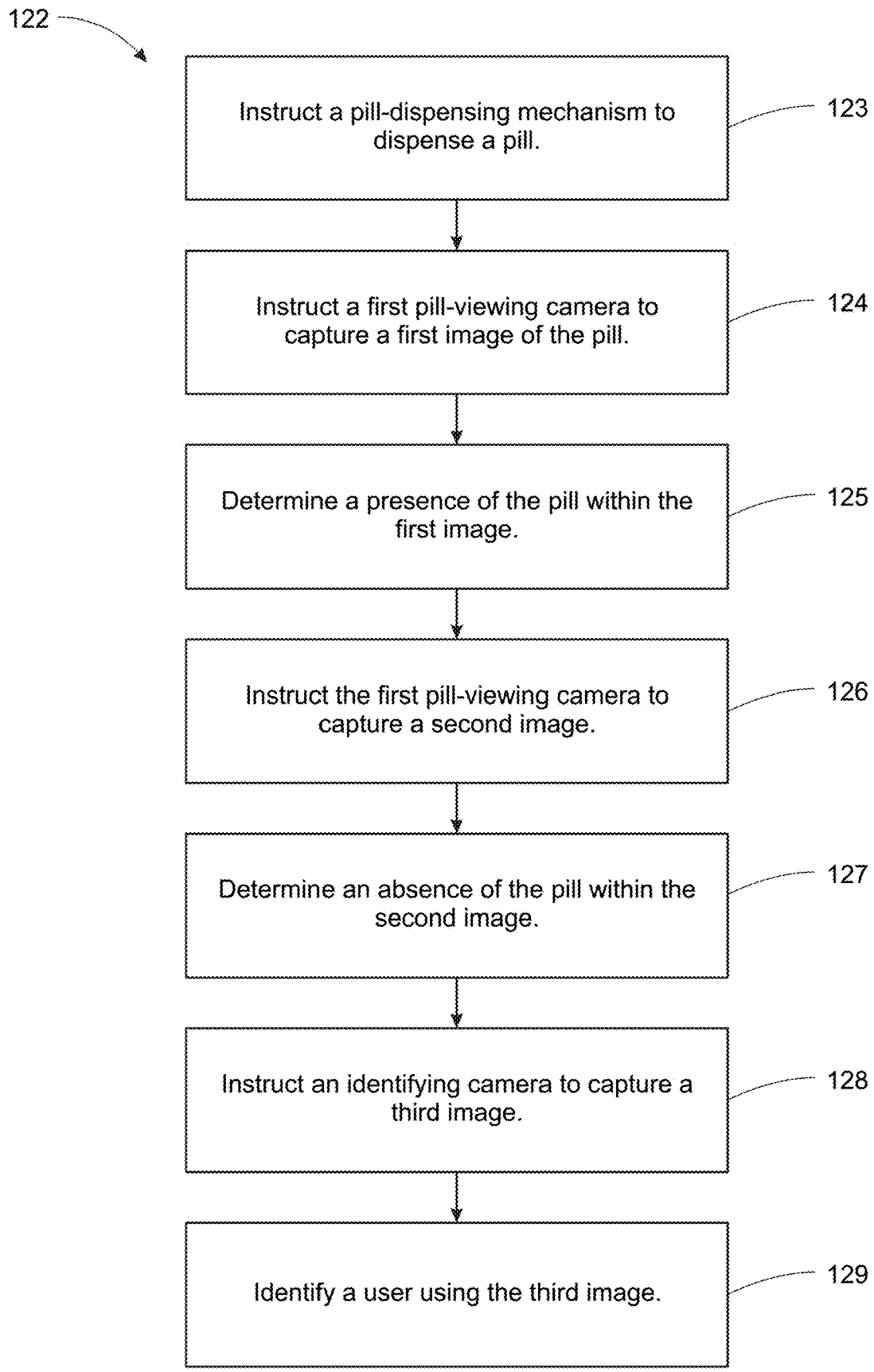
FIG. 16 shows a flow chart diagram of a method for dispensing a pill in accordance with an embodiment of the present disclosure

FIG. 16 shows a flow chart diagram of a method 122 for dispensing a pill in accordance with an embodiment of the present disclosure. The pill dispenser of method 122 may be any sufficient pill dispenser disclosed herein. The method 122 includes acts 123-129.

Act 123 instructs a pill-dispensing mechanism to dispense a pill. Act 124 instructs a first pill-viewing camera to capture a first image of the pill. Act 125 determines a presence of the pill within the first image. Act 126 instructs the first pill-viewing camera to capture a second image. Act 127 determines an absence of the pill within the second image. Act 128 instructs an identifying camera to capture a third image. Act 129 identifies a user using the third image.

A number of implementations have been described. Nevertheless, it will be understood that various modifications may be made. Accordingly, other implementations are within the scope of the following claims. For example, while various principles have been described herein, it is to be understood by those skilled in the art that this description is made only by way of example and not as a limitation as to the scope of the disclosure. Other embodiments are contemplated within the scope of the present disclosure in addition to the embodiments shown and described herein. Modifications and substitutions by one of ordinary skill it the art are considered to be within the scope of the present disclosure.

What is claimed:

1. A pill dispenser, comprising:
    a housing defining an opening;
    a shelf;
    a pill-dispensing mechanism disposed within the housing, the pill-dispensing mechanism configured to dispense a pill to the shelf;
    a pill viewing area operatively coupled to the pill-dispensing mechanism;
    a first pill-viewing camera positioned to capture a first image of the pill viewing area including the shelf;
    a second pill-viewing camera positioned to capture a second image of the pill through a transparent bottom of a cup configuring to receive the pill from the pill viewing area;
    at least one processor in operative communication with the pill-dispensing mechanism and the first pill-viewing camera; and
    a storage medium for storing processor executable instructions configured for execution by the at least one processor for:
        instructing the pill-dispensing mechanism to dispense a pill to the pill viewing area;
        instructing the first pill-viewing camera to capture the first image of the pill;
        instructing the second pill-viewing camera to capture the second image of the pill; and
        identifying the pill using the first and second images.

2. The pill dispenser according to claim 1, wherein the at least one processor identifies the pill using at least one of a color of the pill, a shape of the pill, characters on the pill, and a plurality of colors of the pill as determined using the first and second images.

3. The pill dispenser according to claim 1, wherein the pill viewing area is internal to the housing.

4. The pill dispenser according to claim 3, further including a storage medium for storing processor executable instructions configured for execution by the at least one processor for dispensing the pill to a pill holding area outside of the housing.

5. The pill dispenser according to claim 1, further comprising a scale, wherein the at least one processor is in operative communication with the scale and receives a weight therefrom, wherein the storage medium further comprises processor executable instructions configured for execution by the at least one processor for identifying the pill based upon, at least in part, an estimated weight of the pill using the scale.

6. The pill dispenser according to claim 5, wherein the at least one processor estimates the weight of the pill by subtracting an estimated weight of the cup.

7. The pill dispenser according to claim 5, wherein the at least one processor does not dispense the pill unless the identity of the pill is determined to be appropriate based on information from at least one of an electronic medical record, a drug error reduction system, or a monitoring client.

8. A pill dispenser, comprising:
    a housing defining an opening;
    a pill viewing area disposed within the housing and operatively coupled to the opening;
    a pill-dispensing mechanism disposed within the housing, the pill-dispensing mechanism configured to dispense a pill into the pill viewing area;
    a door mechanism associated with the pill viewing area, wherein the door mechanism is configured to hold the pill within the pill viewing area and dispense the pill through the opening;
    a pill-viewing camera positioned to capture an image of the pill viewing area;
    a second pill-viewing camera positioned to capture a second image of the pill through a transparent bottom of a cup configured to receive the pill from the pill viewing area;
    at least one processor in operative communication with the pill-dispensing mechanism, the pill-viewing camera, and the door mechanism; and
    a storage medium for storing processor executable instructions configured for execution by the at least one processor for:
        instructing the pill-dispensing mechanism to dispense a pill to the pill viewing area;
        instructing the pill-viewing camera to capture the image of the pill;
        verifying the pill using the image;
        instructing the door mechanism to dispense the pill from the pill viewing area through the opening after the pill is verified using the image; and
        instructing the second pill-viewing camera to capture the second image of the pill.

9. The pill dispenser according to claim 8, wherein the at least one processor identifies the pill using at least one of a color of the pill, a shape of the pill, characters on the pill, and a plurality of colors of the pill as determined using the image.

10. The pill dispenser according to claim 8, wherein the pill viewing area is internal to the housing.

11. The pill dispenser according to claim 8, further including a storage medium for storing processor executable instructions configured for execution by the at least one processor for dispensing the pill to a pill holding area outside of the housing.

12. The pill dispenser according to claim 10, further comprising a scale, wherein the at least one processor is in operative communication with the scale and receives a weight therefrom, wherein the storage medium further comprises processor executable instructions configured for execution by the at least one processor for identifying the pill based upon, at least in part, an estimated weight of the pill using the scale.

13. The pill dispenser according to claim 12, wherein the at least one processor estimates the weight of the pill by subtracting an estimated weight of the cup.

14. The pill dispenser according to claim 12, wherein the at least one processor does not dispense the pill unless the identity of the pill is determined to be appropriate based on information from at least one of an electronic medical record, a drug error reduction system, or a monitoring client.

* * * * *